US012807938B2

(12) United States Patent
Drmanac et al.

(10) Patent No.: US 12,807,938 B2
(45) Date of Patent: Nov. 24, 2026

(54) NICK-LIGATE STLFR

(71) Applicant: MGI Tech Co., Ltd., Shenzhen (CN)

(72) Inventors: Radoje T. Drmanac, Los Altos Hills, CA (US); Brock A. Peters, San Jose, CA (US); Andrei Alexeev, Woodland, CA (US); Snezana Drmanac, Los Altos Hills, CA (US); Amulya Nanisetti, Fremont, CA (US)

(73) Assignee: MGI Tech Co., Ltd., Shenzhen (CN)

( * ) Notice: Subject to any disclaimer, the term of this patent is extended or adjusted under 35 U.S.C. 154(b) by 495 days.

(21) Appl. No.: 18/575,985

(22) PCT Filed: Jul. 22, 2022

(86) PCT No.: PCT/CN2022/107241
§ 371 (c)(1),
(2) Date: Jan. 2, 2024

(87) PCT Pub. No.: WO2023/001262
PCT Pub. Date: Jan. 26, 2023

(65) Prior Publication Data

US 2024/0240174 A1 Jul. 18, 2024

Related U.S. Application Data

(60) Provisional application No. 63/224,731, filed on Jul. 22, 2021.

(51) Int. Cl.
*C12Q 1/6855* (2018.01)
*C12N 15/10* (2006.01)

(52) U.S. Cl.
CPC ..... *C12N 15/1065* (2013.01); *C12N 15/1068* (2013.01)

(58) Field of Classification Search
None
See application file for complete search history.

(56) References Cited

U.S. PATENT DOCUMENTS

2017/0355981 A1 12/2017 Jiang et al.

FOREIGN PATENT DOCUMENTS

| | | | |
|---|---|---|---|
| CN | 110520542 | A | 11/2019 |
| CN | 111295443 | A | 6/2020 |
| JP | 2010500002 | A | 1/2010 |
| JP | 2020511966 | A | 4/2020 |
| WO | 2016058517 | A1 | 4/2016 |
| WO | 2019089959 | A1 | 5/2019 |
| WO | 2019236726 | A1 | 12/2019 |
| WO | 2020157684 | A1 | 8/2020 |
| WO | 2020185967 | A1 | 9/2020 |

OTHER PUBLICATIONS

European Application No. 22845425.2, Partial Supplementary European Search Report mailed on Apr. 15, 2025, 13 pages.
Wang et al., Efficient and Unique Cobarcoding of Second-Generation Sequencing Reads from Long DNA Molecules Enabling Cost-Effective and Accurate Sequencing, Haplotyping, and de novo Assembly, Genome Research, vol. 29, No. 5, Apr. 2, 2019, pp. 798-808.
International Application No. PCT/CN2022/107241, International Search Report and Written Opinion mailed on Sep. 28, 2022, 8 pages.
European Application No. 22845425.2, Extended European Search Report mailed on Jul. 8, 2025, 11 pages.

*Primary Examiner* — Christopher M Gross
(74) *Attorney, Agent, or Firm* — Kilpatrick Townsend & Stockton LLP

(57) ABSTRACT

This application relates to methods and compositions for preparing a library of polynucleotides for sequencing comprises in a single reaction mixture. The method comprises contacting a double-stranded target nucleic acid with one or more nicking agents to produce overlapping nucleic acid fragments separated by staggered single-stranded breaks; and contacting a partially double-stranded first adapter with at least one of the nucleic acid fragments in the presence of a ligase, thereby ligating the 5' terminus of the double-stranded region of the first adapter to the 3' terminus of the at least one of the nucleic acid fragments using a DNA ligase via 3' branch ligation. The first adapter comprises (i) a double-stranded blunt end having a 5' terminus and a 3' terminus and (ii) a single-stranded region comprising a barcode.

37 Claims, 18 Drawing Sheets

Specification includes a Sequence Listing.

Two rounds of Nick-ligate
With masterase

Two rounds of Nick-ligate
With Segmentase

SEQUENCE LISTING

```
Sequence total quantity: 5
SEQ ID NO: 1            moltype = DNA  length = 17
FEATURE                 Location/Qualifiers
misc_feature            1..17
                        note = primer
source                  1..17
                        mol_type = other DNA
                        organism = synthetic construct
SEQUENCE: 1
tgtgagccaa ggagttg                                         17
```

-continued

```
SEQ ID NO: 2          moltype = DNA  length = 19
FEATURE               Location/Qualifiers
misc_feature          1..19
                      note = primer
source                1..19
                      mol_type = other DNA
                      organism = synthetic construct
SEQUENCE: 2
gcctccctcg cgccatcag                                            19

SEQ ID NO: 3          moltype = DNA  length = 96
FEATURE               Location/Qualifiers
misc_feature          1..96
                      note = barcode oligonucleotide
source                1..96
                      mol_type = other DNA
                      organism = synthetic construct
SEQUENCE: 3
gtgcactgac gacatgatca ccaaggatcg ccatagtcca tgctaggaag gcgcagacca  60
gagcaactcc ttggctcaca yaaaaaaaaa aaaaaa                         96

SEQ ID NO: 4          moltype = DNA  length = 13
FEATURE               Location/Qualifiers
misc_feature          1..13
                      note = hybridization oligonucleotide
source                1..13
                      mol_type = other DNA
                      organism = synthetic construct
SEQUENCE: 4
gtcgtcngtg can                                                  13

SEQ ID NO: 5          moltype = DNA  length = 29
FEATURE               Location/Qualifiers
misc_feature          1..29
                      note = L-oligo
source                1..29
                      mol_type = other DNA
                      organism = synthetic construct
SEQUENCE: 5
gagacgttct cgactcagca gannnnnnn                                 29
```

NICK-LIGATE STLFR

RELATED APPLICATION

This application is a national phase application of PCT Application No. PCT/CN2022/107241, filed Jul. 22, 2022, which claims priority to and the benefit of U.S. Provisional Application No. 63/224,731, filed on Jul. 22, 2021. The entire content of said provisional application and said PCT application is herein incorporated by reference for all purposes.

REFERENCE TO AN ELECTRONIC SEQUENCE LISTING

The contents of the electronic sequence listing (106340-1409823-5100-US SL.xml; Size: 8 KB; and Date of Creation: Oct. 30, 2023) is herein incorporated by reference in its entirety.

BACKGROUND

Constructing sequencing libraries for commonly used next-generation sequencing platforms often requires adding adapters to both ends of the target nucleic acids. These adapters typically contain barcodes for sample or molecule identification. In some cases, co-barcoding is implemented to add the same barcode to sub-fragments of single long genomic DNA molecules to facilitate whole-genome sequencing. The current processes of construction of sequencing libraries often require multi-step procedures to add adapters. Each of the steps are often carried out in separate reactions or vessels, which can be labor-intensive and inefficient.

SUMMARY OF INVENTION

In one aspect, this disclosure provides a method for preparing a library of adaptered polynucleotides for sequencing, comprising, in a single reaction mixture: (a) contacting a double-stranded target nucleic acid with one or more nicking agents to produce a plurality of overlapping nucleic acid fragments separated by staggered single-stranded breaks; (b) providing a plurality beads each comprising a plurality of branch ligation adapters immobilized on beads (b-BLAs) and providing population of L-adapters with a degenerate sequence at the 3' terminus and (c) contacting the b-BLAs with at least one of the nucleic acid fragments in the presence of a ligase, whereby ligating the b-BLAs to the 3' terminus of the nucleic acid fragments, (d) contact the population of L-adapters in the presence of a ligase thereby ligating the L-adapters to the 5' terminus of the nucleic acid fragments, thereby obtaining a library of nucleic acid fragments having the L-adapter sequence at the 5' terminus and the b-BLA adapter sequence at the 3' terminus.

In another aspect, disclosed herein is a method for preparing a library of polynucleotides for sequencing comprises in a single reaction mixture:

(a) contacting a double-stranded target nucleic acid with one or more nicking agents to produce overlapping nucleic acid fragments separated by staggered single-stranded breaks; and (b) contacting a bead comprising a plurality of partially double-stranded first adapters with the nucleic acid fragments in the presence of a ligase, wherein each first adapter comprises (i) a double-stranded blunt end comprising a 5' terminus of one strand and a 3' terminus of the complementary strand and (ii) a single-stranded region that is immobilized on a bead, wherein the single-stranded region comprises a barcode, thereby ligating the 5' terminus of the strand in the double-stranded blunt end of at least one first adapters to the 3' terminus of the at least one of the nucleic acid fragments using a DNA ligase to produce a ligated first adapter, wherein the ligated first adapter comprises the barcode and at least one nucleic acid fragment, (c) denaturing the ligated first adapter, and (d) performing a controlled extension of a primer hybridized to a sequence that is 3' relative to the barcode in the ligated first adapter thereby producing a partially extended strand complementary to the ligation first adapter.

In yet another aspect, disclosed herein is a reaction mixture comprising (1) one or more nicking agents, (2) one or more ligases, (3) a plurality of overlapping nucleic acid fragments separated by staggered single-stranded breaks, and (4) a partially double-stranded branch adapter comprising a barcode oligonucleotide and hybridization oligonucleotide hybridized to each other to form partially double-stranded nucleic acid molecule, wherein the barcode oligonucleotide is joined to a bead and comprises a barcode, wherein the hybridization oligonucleotide is not joined to the bead, wherein the partially double-stranded nucleic acid molecule comprises (i) a double-stranded blunt end having a 5' terminus and a 3' terminus and (ii) a single-stranded region comprising the barcode and having a single-stranded end, wherein the 5' terminus of the double-stranded blunt end is ligated to a 3' terminus of at least one of the nucleic acid fragments.

BRIEF DESCRIPTION OF THE DRAWINGS

The drawings and descriptions thereof illustrate exemplary embodiments of the invention. The inventions provided in this disclosure are not limited to the embodiments shown in these drawings.

FIG. 2 also illustrates extending the breaks to creator extending the gap (230) between the fragments (240) separated by the breaks to prepare for ligation of adapters.

FIG. 3A shows that a bead (300) comprise b-BLAs immobilized thereon. Each b-BLA consists of two strands: 1) a barcode oligonucleotide comprising a barcode sequence (330) and a dideoxy blocker nucleotide at the 3' end, and 2) a hybridization oligonucleotide, which is hybridized to the barcode oligonucleotide. The 5' of the barcode oligonucleotide is joined to the bead (300). Although shown in separate steps for better illustration and explanation, the addition of the b-BLA adapter and L-adapter can occur in one single reaction. The barcode (330) from the b-BLA adapter (340) was copied by extending the strand (350) that is not joined to the bead, which produces an extended nucleic acid fragment (360). Excess b-BLA adapters (370) (i.e., b-BLA adapters that are not ligated to a fragment) will also be extended. The extended nucleic acid fragment (360) can be amplified using two primers annealed to the b-BLA adapter sequence and the L-adapter sequence at the two termini.

Alternatively, the extended nucleic acid fragment (360) can be circularized by using a split oligo that anneals to both adapter sequences, as further described below. See section 10 entitled "Amplification". The excess adapters (370) do not have an L-adapter and thus cannot be amplified by PCR or circularized.

Figure 4:
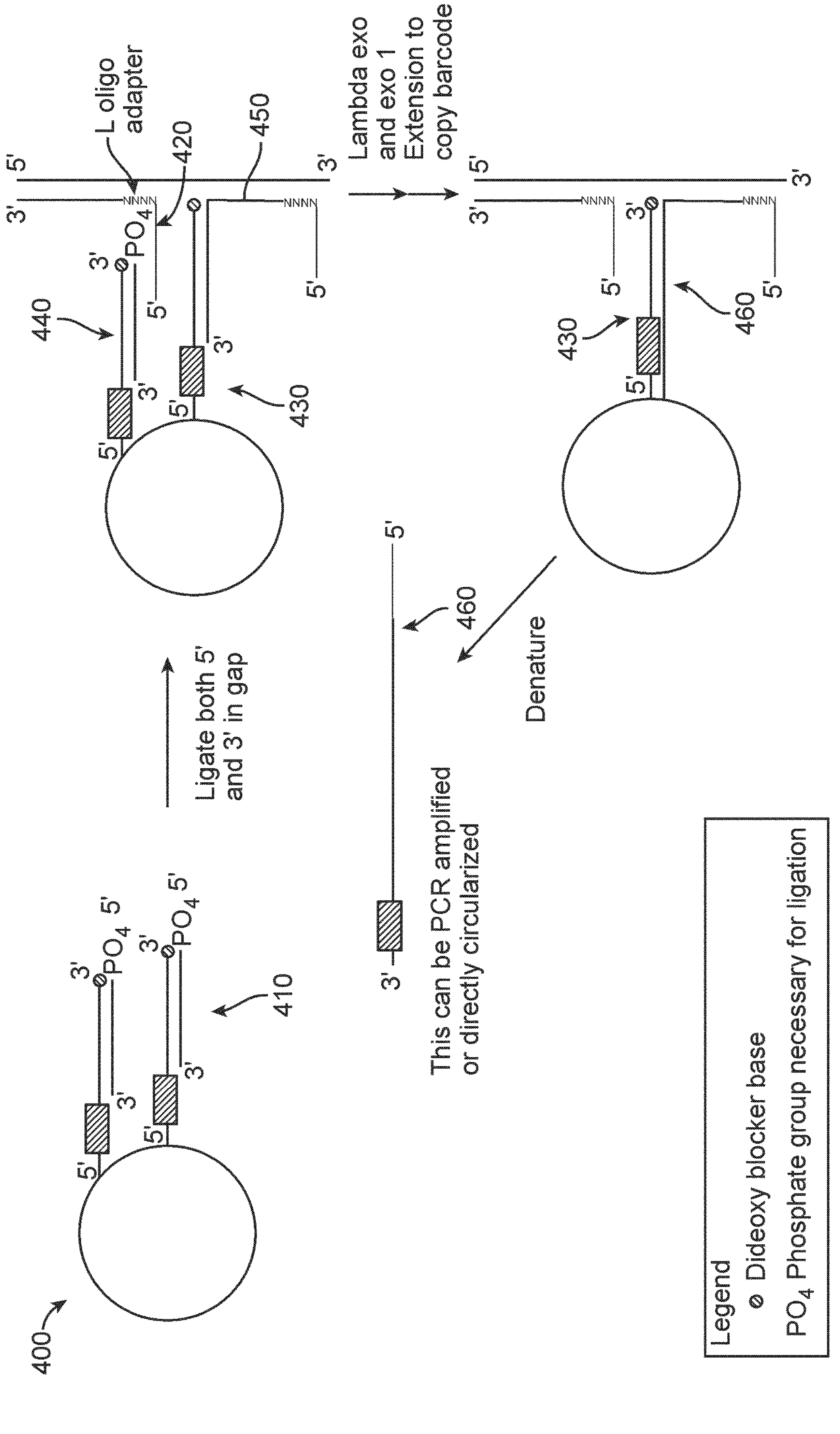

FIG. 4 shows an exemplary method of adding a b-BLA (410) to the 3' and an L-adapter (420) to the 5' of the target DNA in one single reaction. The L-adapters comprises protected bond (for example, a (phosphorothioate bond or the like) to prevent exonuclease digestion (indicated by *) The barcode oligonucleotide of each b-BLA is blocked at the 3 end (e.g., by having a dideoxy blocker nucleotide). The hybridization oligonucleotide of the same b-BLA can be ligated to the target nucleic acid fragments through 3' branch ligation. The ligated product (450) formed by ligating the hybridization oligonucleotide and the target nucleic acid fragment is extended to incorporate the barcode (430) from the b-BLA to form an extended nucleic acid fragment (460). The extended nucleic acid fragment (460) can be released from the bead by denaturing, and the released fragment is then amplified by PCR or circularized. Optionally, excess b-BLA (440) can be degraded by a Lambda exonuclease and an exonuclease to avoid amplifying unligated adapters.

Figure 5:
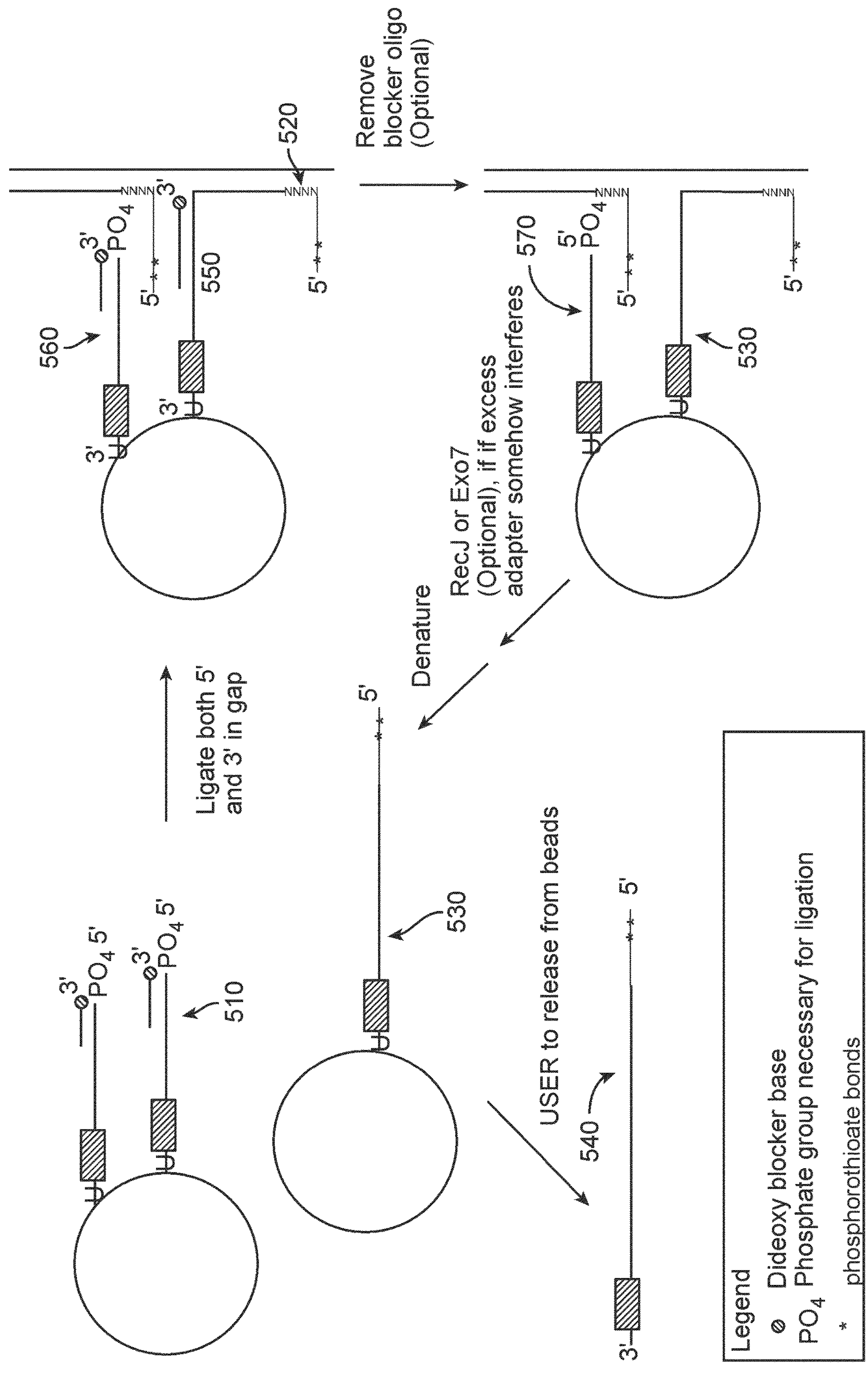

FIG. 5 shows another exemplary method of adding a b-BLA (510) to the 3' and adding an L-adapter (520) to the 5' of the target DNA in one single reaction similar to what is shown in FIG. 4. The b-BLAs are immobilized on beads (500). Unlike FIG. 4, wherein the barcode oligonucleotide is blocked from being extended, in FIG. 5, the hybridization oligonucleotide is blocked and the barcode oligonucleotide can be ligated to the target nucleic acid fragment to produce barcoded nucleic acid fragment (550); there is no need to copy the barcode by extension. Then, both the excess b-BLA (560) and the ligated product are denatured, which results in single-stranded barcoded nucleic acid fragment (530), which remains joined to the bead. In one approach, the b-BLA comprises uracils near the 3' end of the barcode oligonucleotide; the barcoded nucleic acid fragment (530) produced as above can be released from the bead by contacting USER. This released strand (540) can then be amplified or directly circularized. Optionally, the excess b-BLAs (570) can be removed by RecJ or Exo7 treatment. The "*" represent the phosphorothioate bonds.

Figure 6:
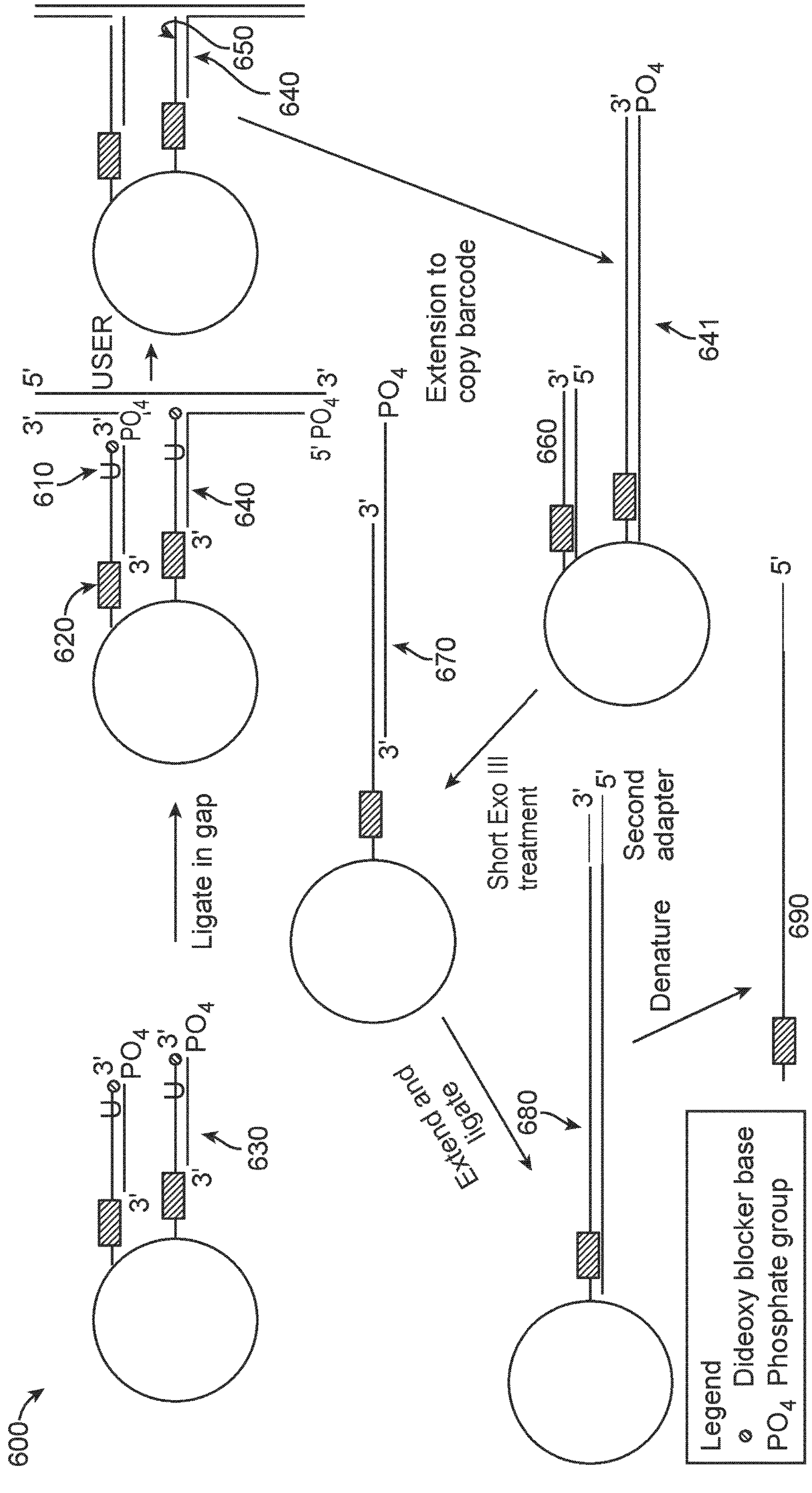

FIG. 6 shows an illustrative embodiment of the invention in which b-BLA are contacted with the target DNAs during the nickase treatment. Similar to FIG. 4, the barcode oligonucleotide of each b-BLA is blocked from being extended; but in FIG. 6, each barcode oligonucleotide may also comprise one or more uracils (610) between the barcode sequence (620) and the dideoxy blocker nucleotide. The hybridization oligonucleotide (630) can be ligated to a target nucleic acid fragment through branch ligation. USER is then added to cleave the barcode oligonucleotide and release the dideoxy blocker nucleotide which results in barcode oligonucleotide having an extendible end (650). The ligated product (630) is extended to incorporate the barcode to form a barcoded nucleic acid fragment (640). The barcode oligonucleotide which is free of the blocker nucleotide at the 3' (650) is also extended. ExoIII, which has 3'→5' exonuclease activity, is then added to completely degrade the excess b-BLA (660) and also partially degrade the barcoded nucleic acid fragment from 3'→5' direction, which results in a partially hybridized barcoded target nucleic acid fragment (670). Said partially hybridized barcoded target nucleic acid fragment (670) is then extended to form a double-stranded barcoded nucleic acid fragment (680), which is then ligated with a second adapter through blunt end ligation. In some cases, the second adapters do not comprise 5' phosphate group to minimize self-ligation. The ligation product is denatured to form a single-stranded nucleic acid fragment (690), which now has adapter sequences at both ends. The single-stranded nucleic acid fragment (690) can now be amplified by PCR or circularized.

Figure 7A:
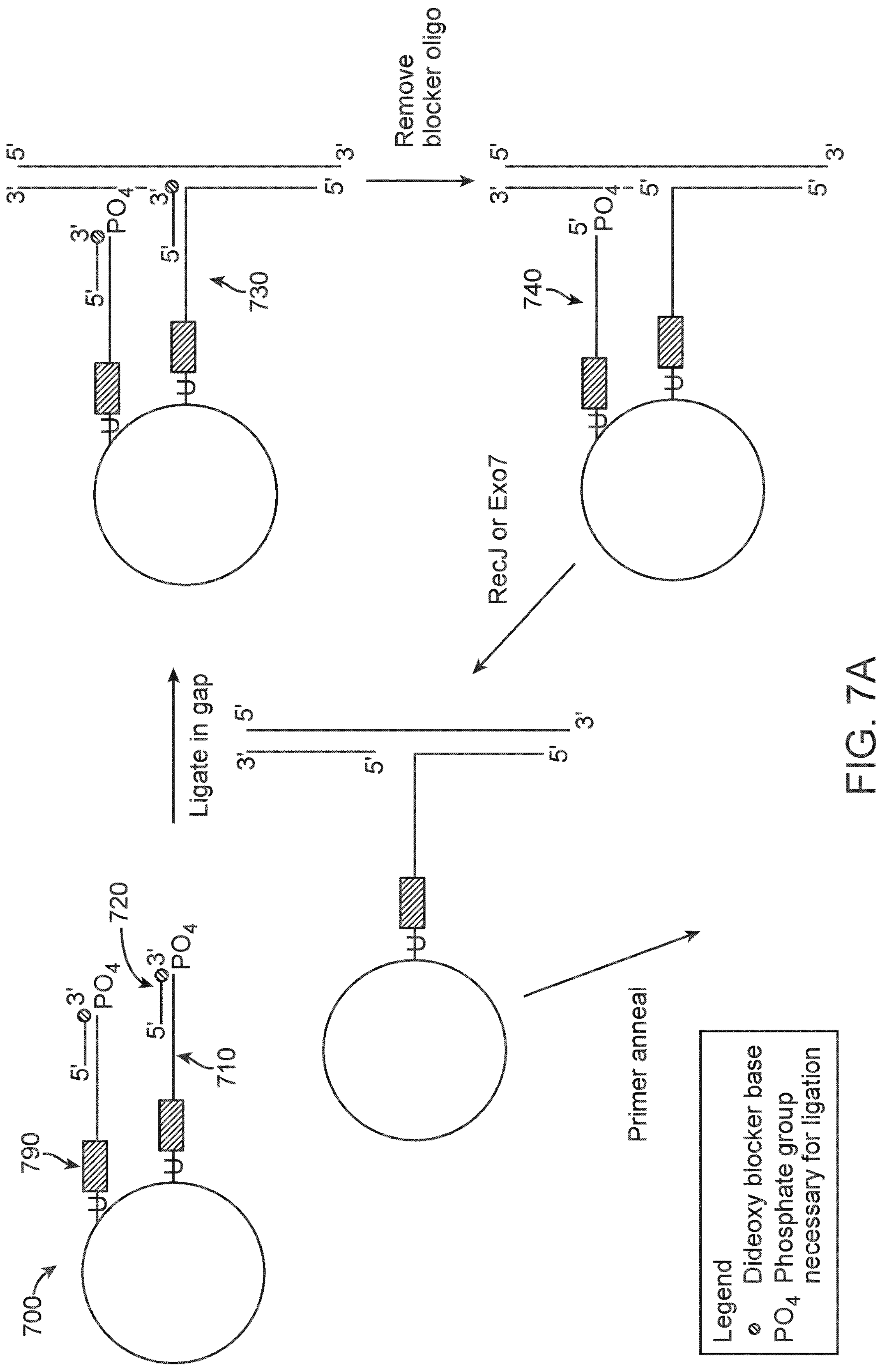
Figure 7B:
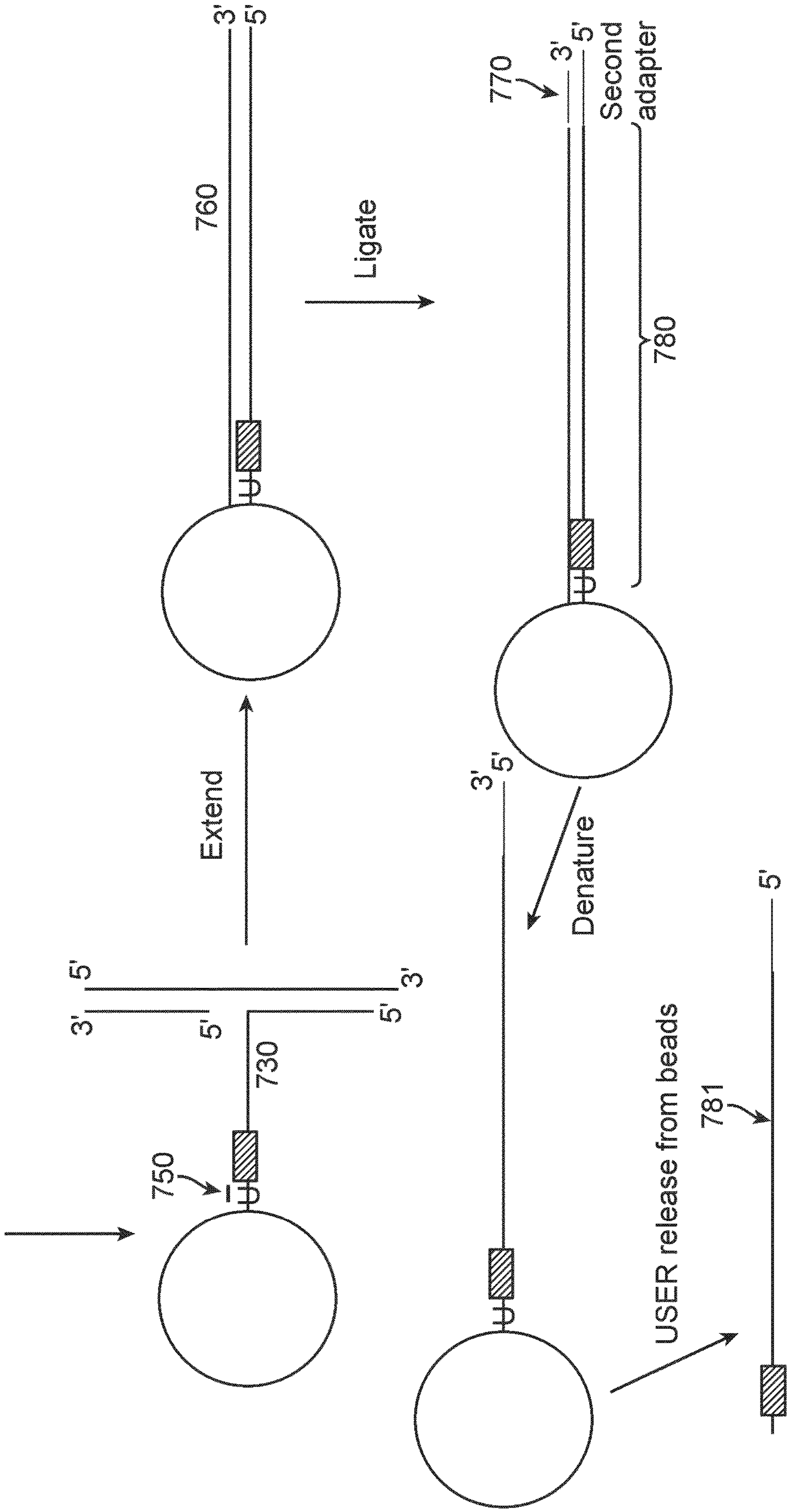

FIGS. 7A and 7B show another embodiment of the invention in which b-BLAs are immobilized to a bead (700). Each b-BLA comprises a barcode oligonucleotide (710) and a hybridization oligonucleotide (720) hybridized to each other. The hybridization oligonucleotide comprises a dideoxy blocker nucleotide at the 3' end, and the barcode oligonucleotide comprises uracils at a locus that is 5' to the barcode sequence (790). FIGS. 7A and 7B illustrate the following events: 1) The barcode oligonucleotide is ligated to the nickase-treated target nucleic acid fragment and form a barcoded nucleic acid fragment (730) through branch ligation. 2) The hybridization oligonucleotide is removed by denaturing; 3) A nuclease such as RecJ or ExoVII is added to degrade the single-stranded excess b-BLA (740); 4) A primer (750) is annealed to a sequence 5' of the barcode on the barcoded nucleic acid fragment (730) and extended to form a double-stranded DNA molecule (760); The double-stranded DNA molecule is then ligated to a second, double-stranded adapter (770) to form a double-stranded molecule (780) with adapter sequences at both ends, one adapter sequence from the branch adapter and the other adapter sequence from the second, double-stranded adapter. Optionally, the second adapter does not comprise a 5' phosphate to avoid self-ligation. The double-stranded molecule (780) with dual-adapter sequences are then denatured and released from the bead by USER, resulting in a single-stranded molecule (781), which can then be amplified and/or circularized.

Figure 8:
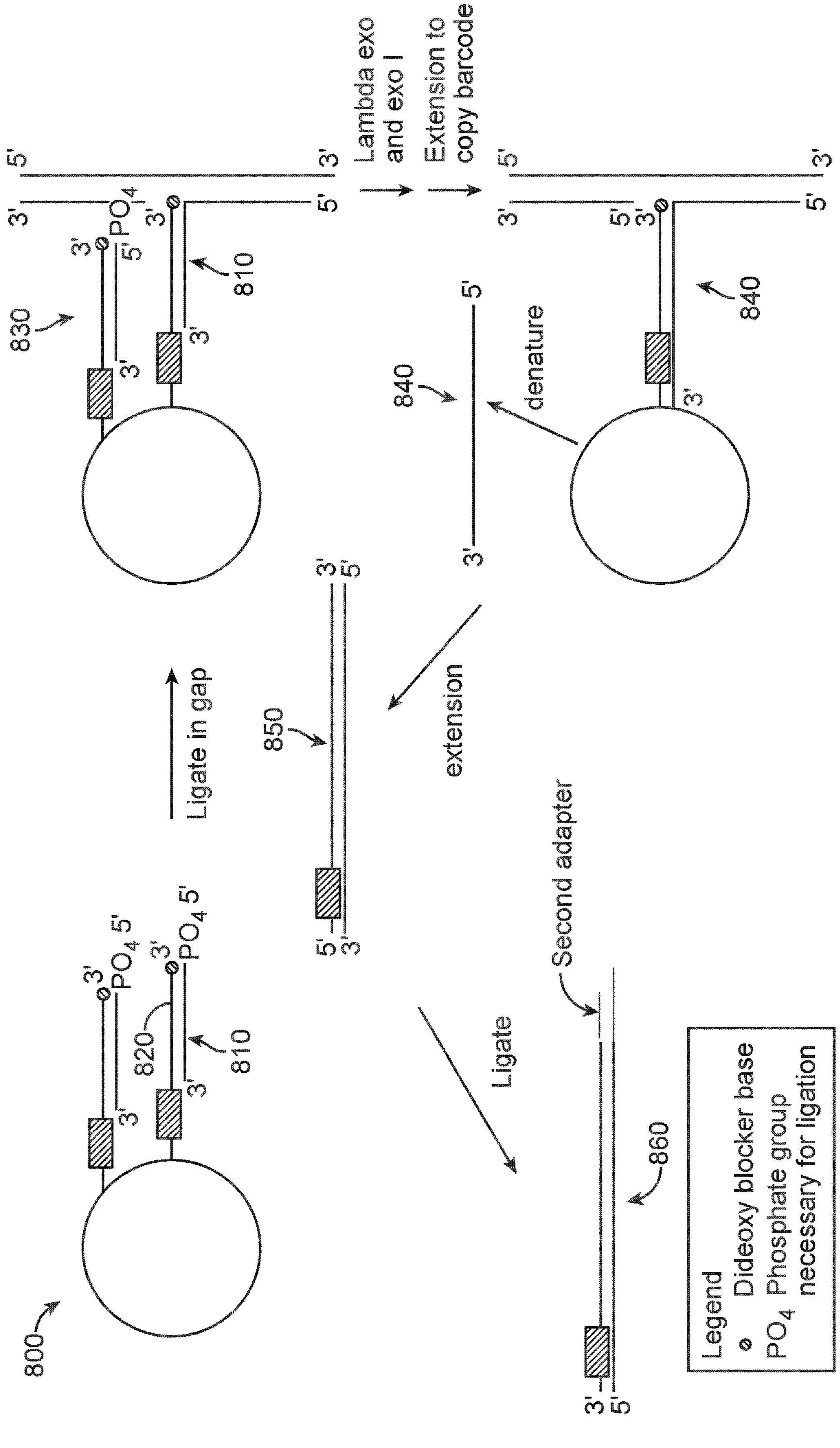

FIG. 8 shows an illustrative embodiment of the invention in which b-BLAs are immobilized to a bead (800). Each b-BLA comprises a barcode oligonucleotide (820) and a hybridization oligonucleotide (810). The barcode oligonucleotide (820) comprises a dideoxy blocker nucleotide at the 3'. The hybridization oligonucleotide in the b-BLA is ligated to the target nucleic acid fragment via branch ligation during the nickase treatment. A lambda exonuclease and exonuclease I is added to the reaction to remove the excess b-BLAs (830). The ligation product formed by ligating the hybridization oligonucleotide and the target nucleic acid fragment is extended to copy the barcode, which results in a barcoded nucleic acid fragment (840), which is separated from the barcode oligonucleotide by denaturing. A primer is annealed to the single-stranded molecule at a sequence 3' to the barcode sequence and extended. The extension forms a double-stranded molecule (850), which is then ligated to a second adapter to form a double-stranded nucleic acid fragment (860) having adapter sequence at both ends. The double-stranded nucleic acid fragment (860) can then be amplified by PCR. Alternatively, the double-stranded nucleic acid fragment can be denatured to form single-stranded nucleic acid fragment, which is then circularized. Optionally, the second adapter lacks a 5' phosphate, which can minimize self-ligation of individual second adapters.

Figure 9A:
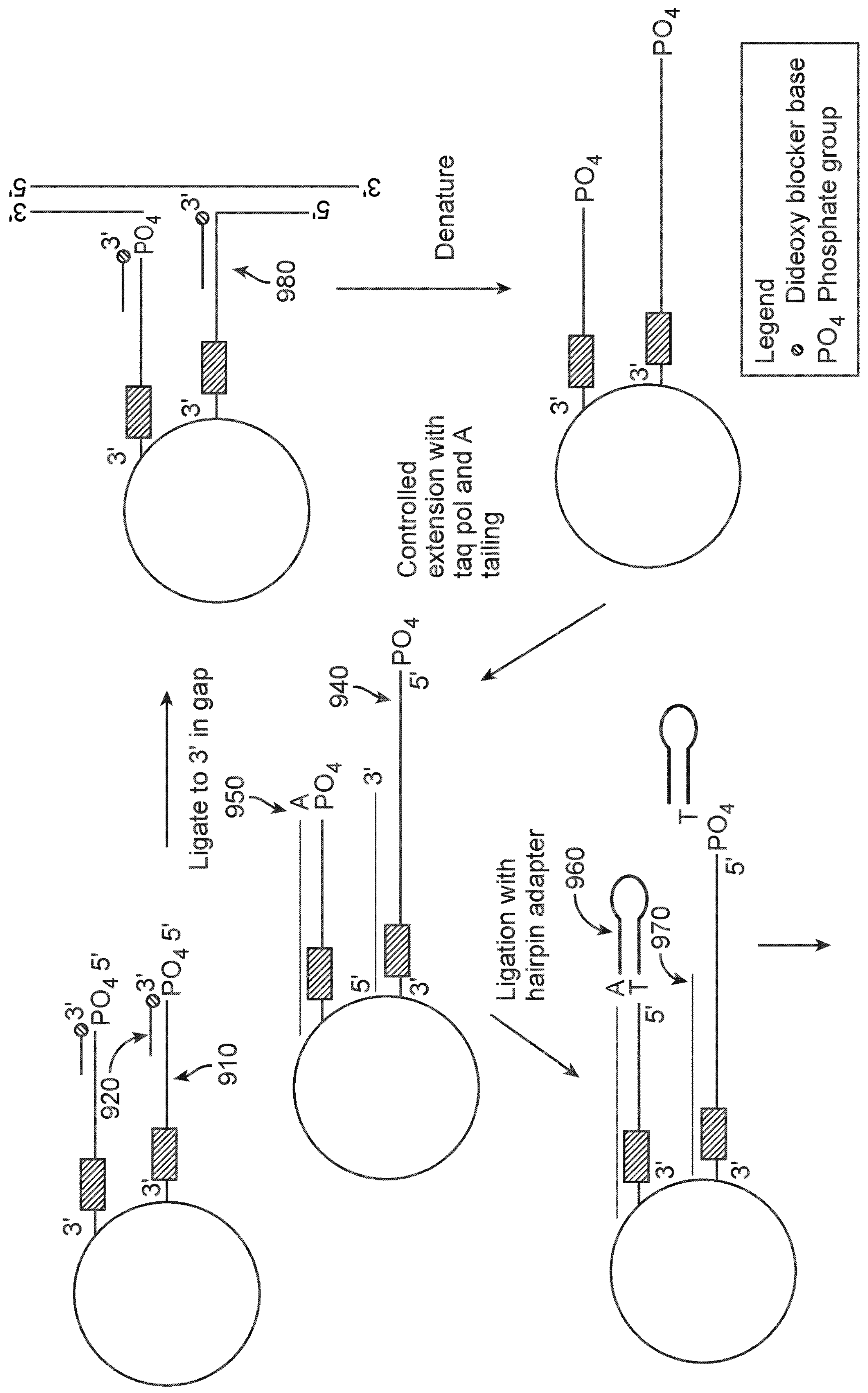
Figure 9B:
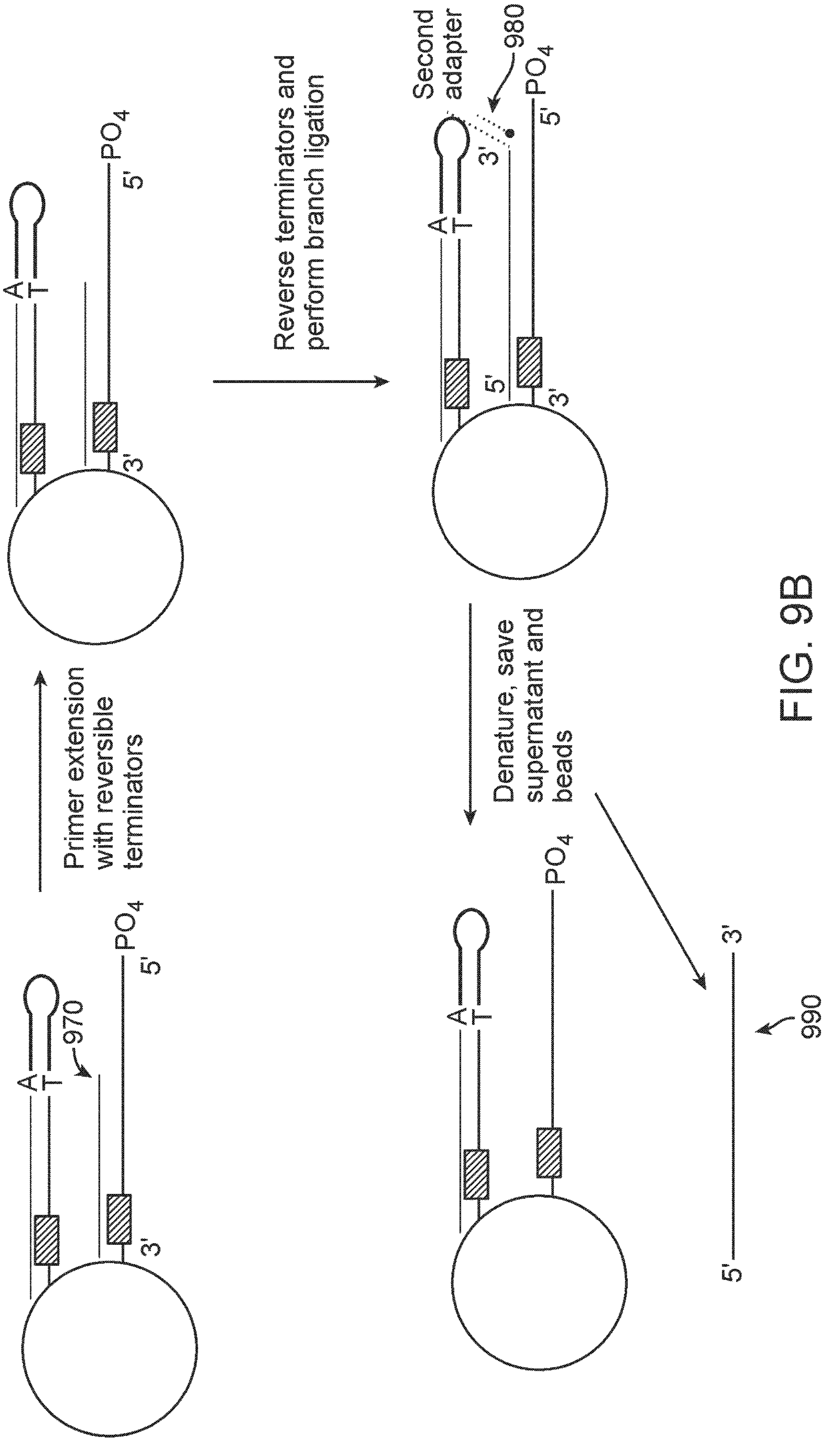

FIG. 9A and FIG. 9B show another embodiment of the invention in which a b-BLAs are immobilized to the bead (900). Each b-BLA comprises a barcode oligonucleotide (910) and a hybridization oligonucleotide (920) hybridized to each other. The hybridization oligonucleotide (920) comprises a dideoxy blocker nucleotide at the 3' end. First, the barcode oligonucleotide is ligated to the nickase-treated target nucleic acid fragment and form a barcoded nucleic acid fragment (930) through branch ligation. Second, the hybridization oligonucleotide is removed by denaturing. Third, a controlled polymerase extension is performed, which leaves a 5' overhang (940) that can be used for 3' branch ligation. The controlled extension only goes about 100-150 bases and is performed by a DNA polymerase that does not have 3-5' exonuclease activity resulting in an A tail (950) at the end of the template. This will cause complete extension and A tailing of excess adapter, but those adapters ligated to genomic fragments will be incomplete. Next, ligation is performed with a hairpin adapter with a T tail complementary to the A tail of the extended excess adapters, resulting the excess adapters (960) being blocked from ligation or extension while the remaining adapters ligated to the target nucleic acid fragments (970) are not blocked (i.e., these remaining adapters are unable to ligate to the hairpin adapters). The terminators can be added at different concentrations or at different time points during different cycles to produce extension products having different length, which can provide overlapping coverage across most of the bases of each fragment during the sequencing process.

The remaining adapters (970) are further extended with reversible terminators, followed by a reaction to remove the terminator blocking group, and then 3' branch ligation is performed to add a second adapter (980) to target nucleic acid fragment at the end. The reaction is then denatured and the single-stranded molecule comprising two adapter sequences at both ends (990) can then be amplified by PCR or circularized.

Figure 10A:
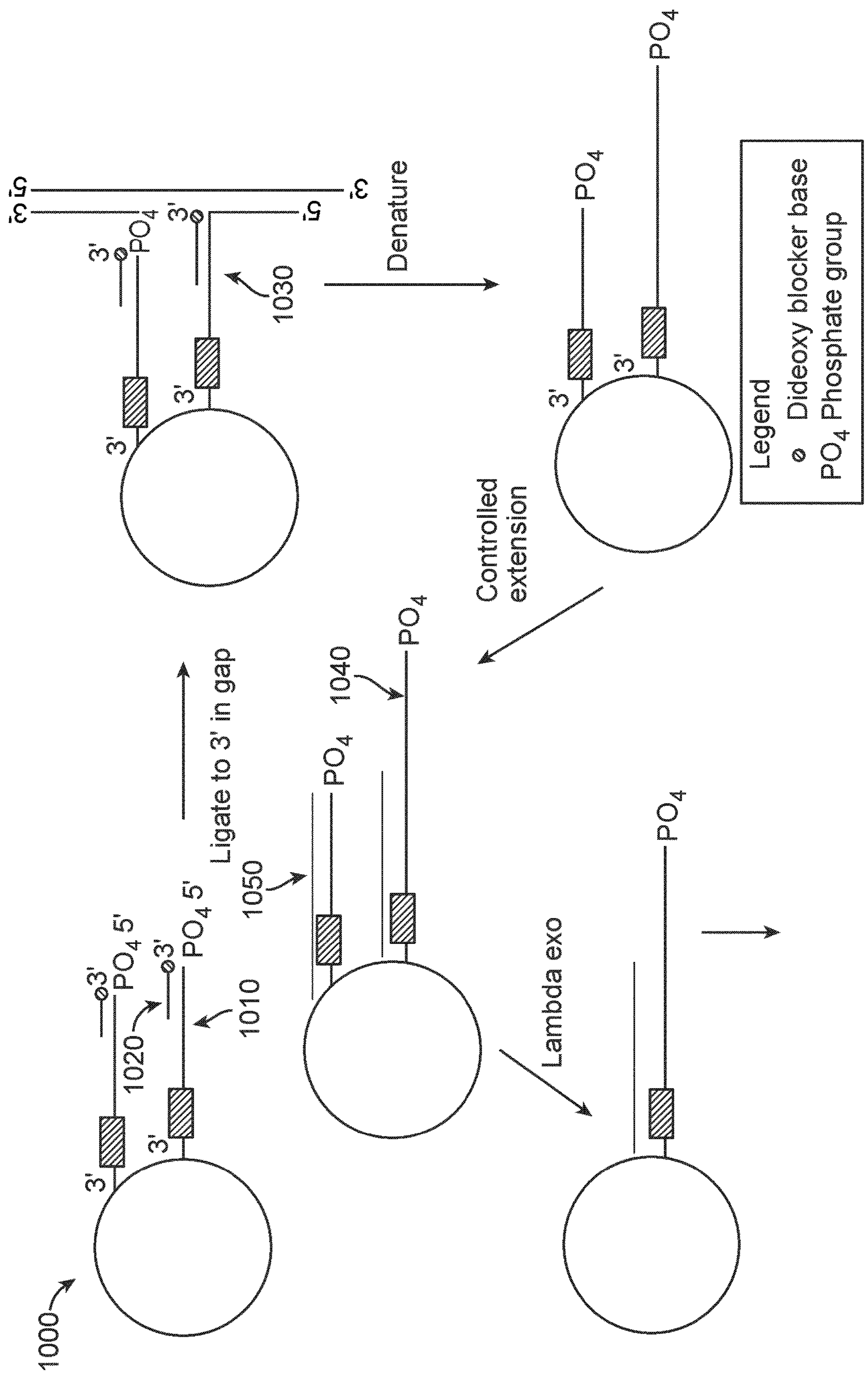
Figure 10B:
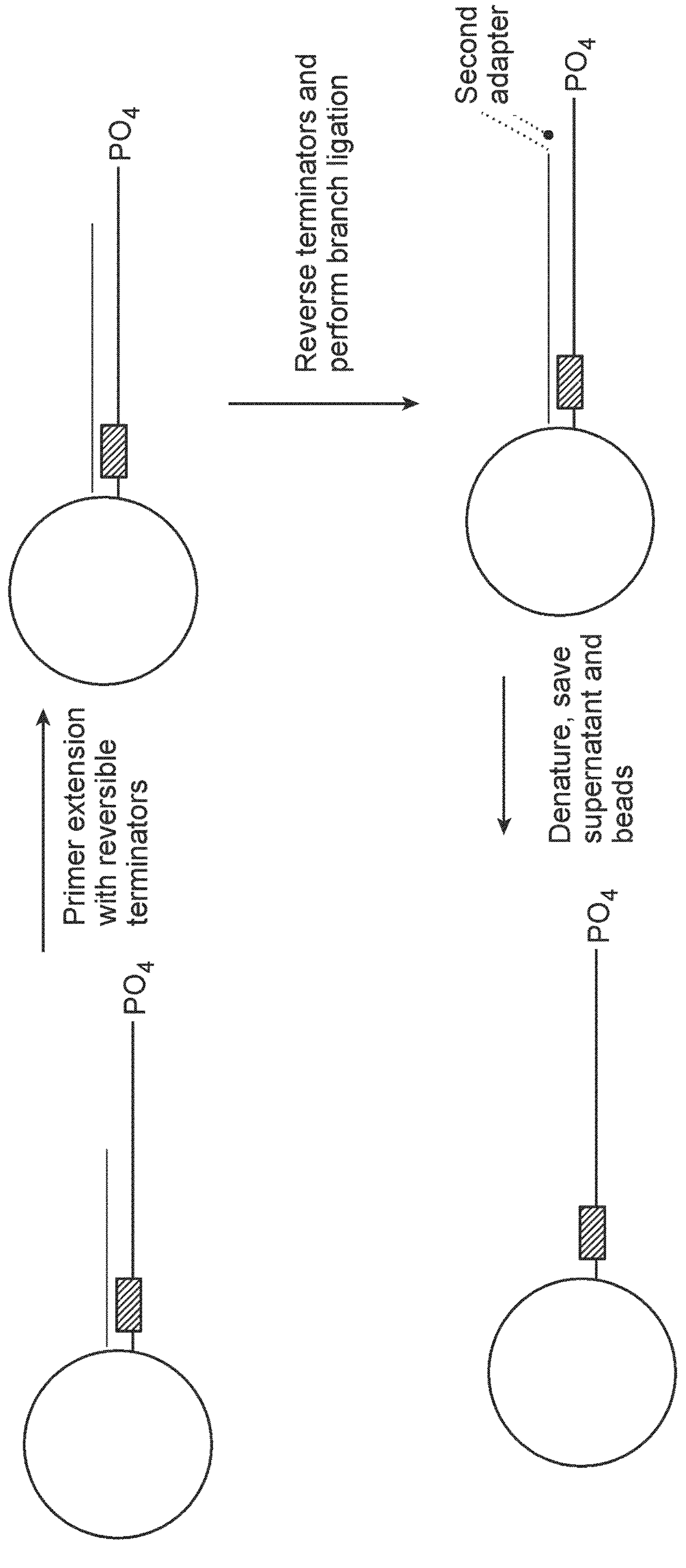

FIG. 10A and FIG. 10B show another embodiment of the invention that involves performing a controlled extension. Similar to FIGS. 9A and 9B. The b-BLA used in this embodiment is also a branch adapter, which comprises a barcode oligonucleotide and a hybridization oligonucleotide (1020) hybridized to each other. The hybridization oligonucleotide (1020) comprises a dideoxy blocker nucleotide at the 3' end. First, the barcode oligonucleotide is ligated to the nickase-treated target nucleic acid fragment and form a barcoded nucleic acid fragment (1030) through branch ligation. Second, the hybridization oligonucleotide is removed by denaturing. Third, a controlled polymerase extension is performed using a polymerase with 3-5' exonuclease activity under conditions to limit the extension to about 100-150 bases. This leaves a 5' overhang (1040) that can be used for 3' branch ligation. This results in an incomplete extension for those adapters ligated to a target nucleic acid fragment (1040) and complete extension for the excess adapters (1050). which form a blunt end dsDNA adapter with a 5' phosphate. A lambda exonuclease is then added to the reaction and Lambda degrades the blunt end dsDNA adapter with the 5' phosphate (1050). Lambda exonuclease prefers phosphorylated double-stranded DNA over single-stranded DNA, so adaptered short inserts (such as 1050) would be preferentially degraded over long DNA inserts (such as 1040). The remaining steps of the method, as shown in FIG. 10B, are similar to those depicted in FIGS. 9A and 9B.

Figure 11A:
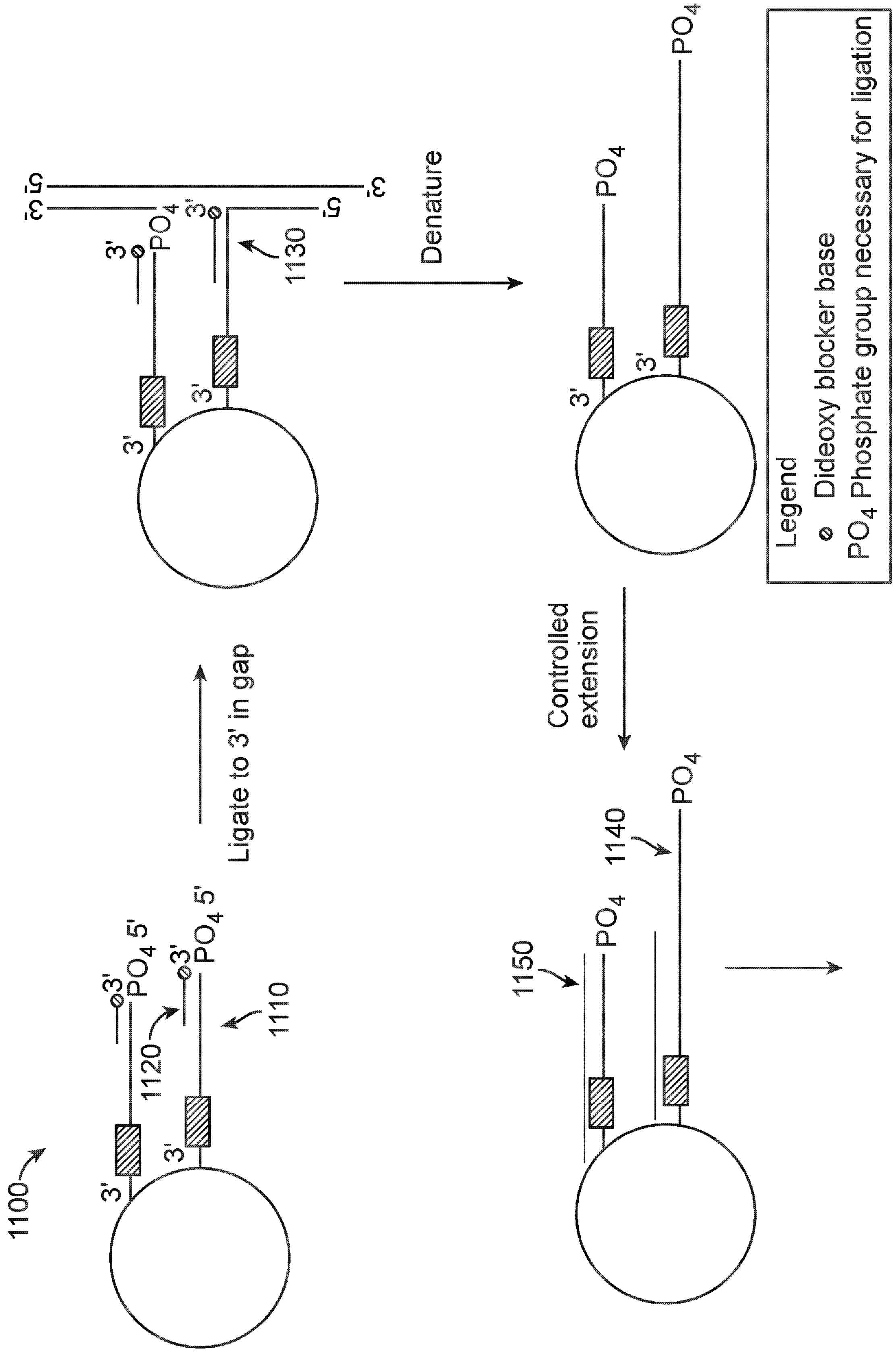
Figure 11B:
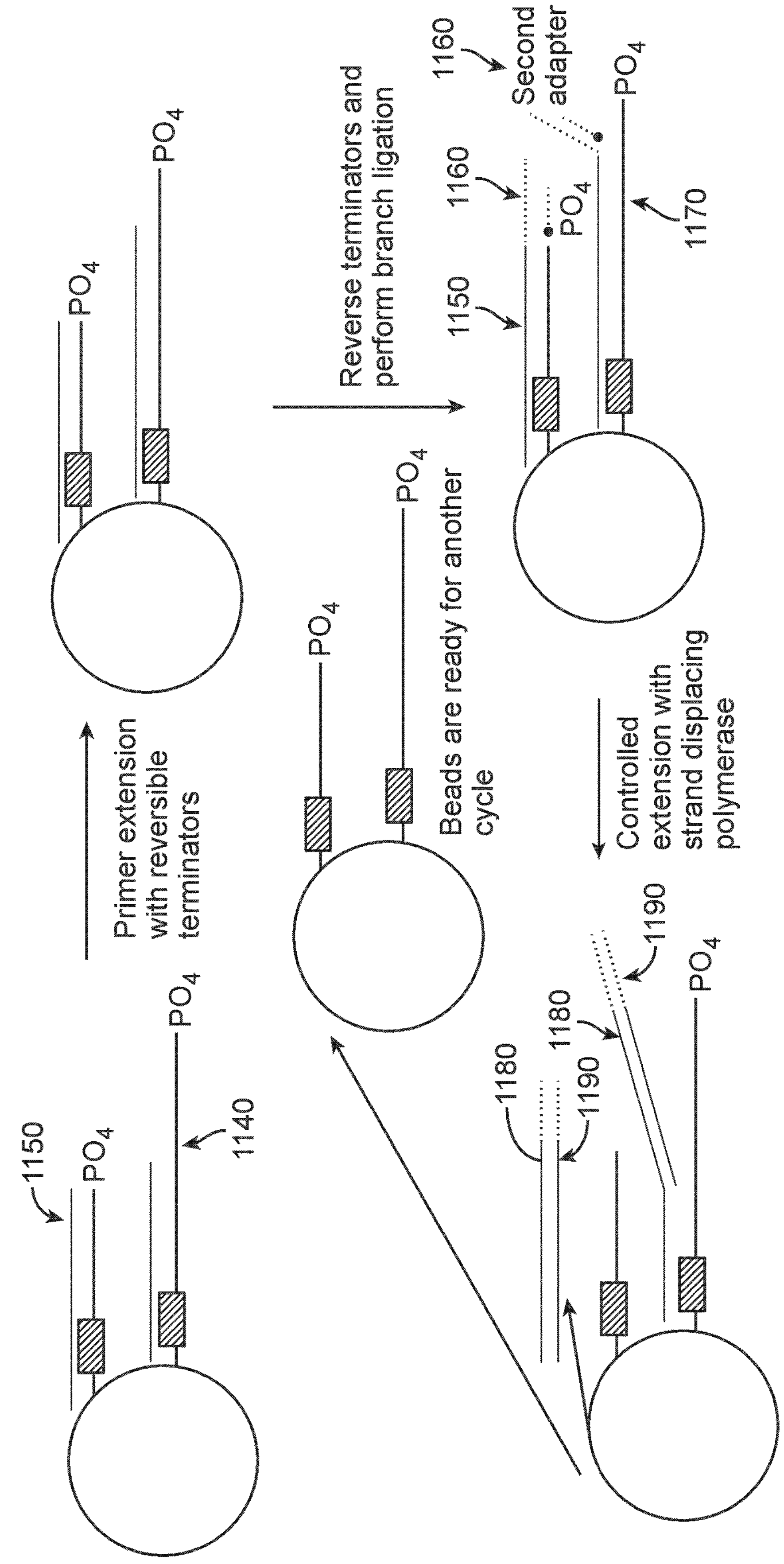

FIG. 11A shows performing controlled extensions as described in FIG. 10A, which fully extend the excess adapters (1150) and partially extend the ligated products (1140). FIG. 11B shows that the partially extended ligation products (1140) are then further extended in the presence of reversible terminators, followed by removal of the terminator blocking group in the reversible terminators, then ligated with a second adapter (1160). This results in the blunt-end ligation of the excess adapter (1150) and 3' branch ligation of the barcoded target nucleic acid fragments (1170) to form a nucleic acid fragment having adapter sequences at both ends (1180). The unligated strand (1190) is extended by a strand displacing polymerase under extension-controlling conditions so that the unligated strand only extends about 100-150 bases. This extension results in the strand displacement of the adaptered nucleic acid fragment that remains immobilized onto the bead and the release of adaptered nucleic acid fragment (1190). The release of adaptered nucleic acid fragment can be collected in the solution. The beads can be reused for the next cycle of controlled extension. Similar to other embodiments described above involving reversible terminators, the terminators can be added at different concentrations or at different time points during different cycles to produce extension products having different length. This advantageously provides overlapping coverage across most of the bases of each fragment during the sequencing process.

Figure 12B:
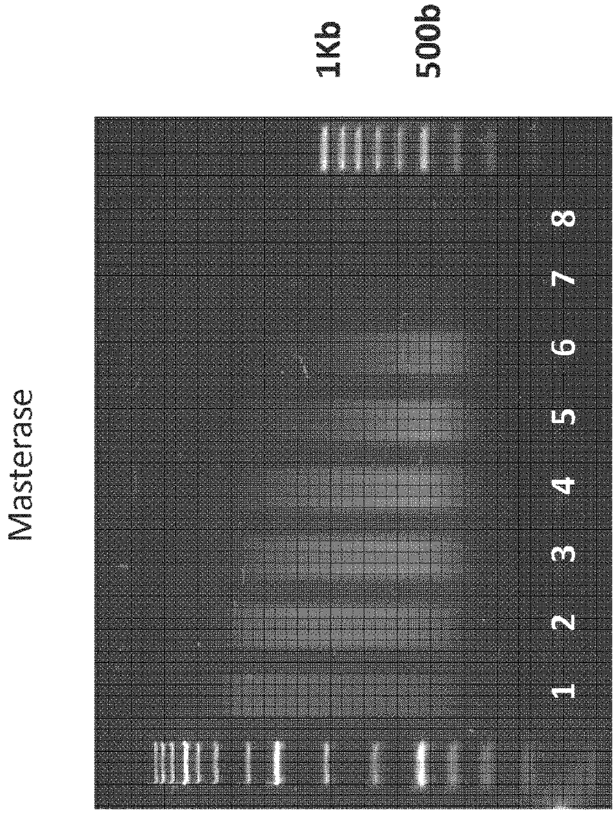
Figure 12A:
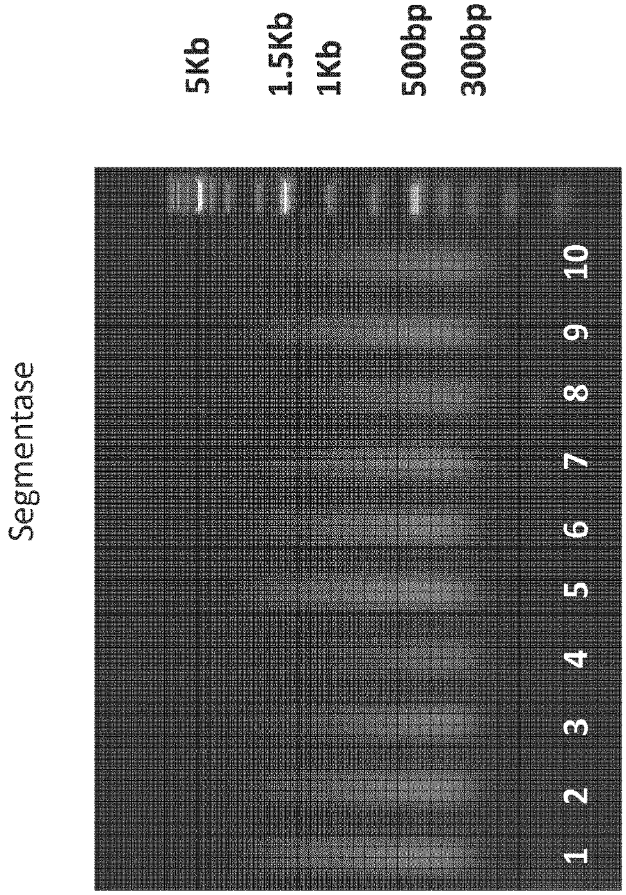
Figure 12D:
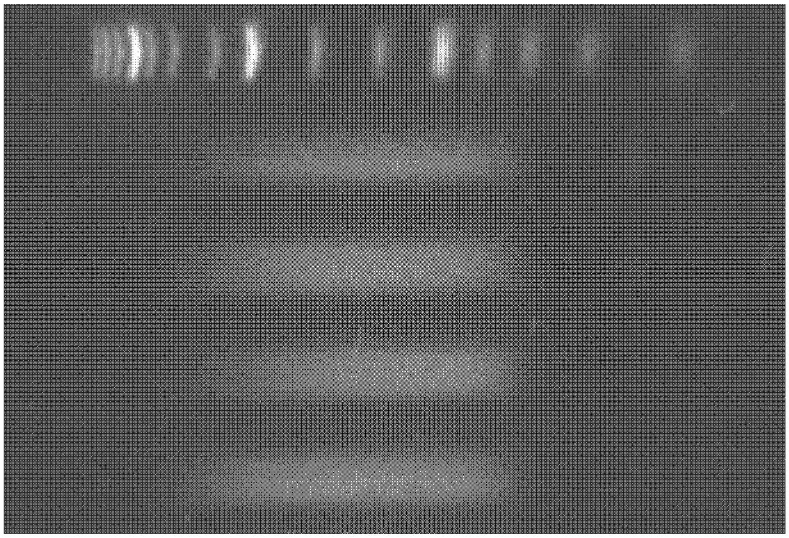
Figure 12C:
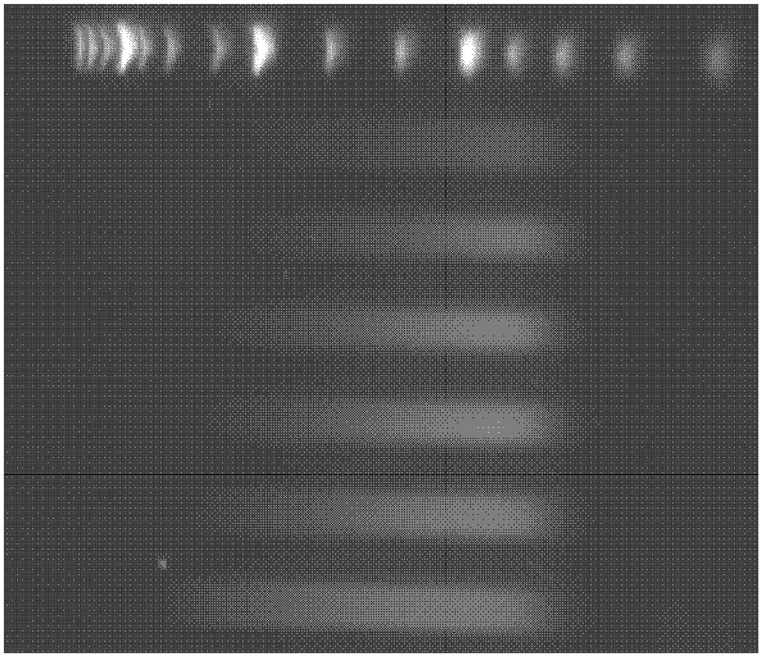

FIG. 12A and FIG. 12B show the results of electrophoresis of nick-ligate products formed using methods disclosed herein. Segmentase (available from MGI, Shenzhen, P.R. China) was used in gradually increasing amounts in different reactions depicted in FIG. 12A, and Masterase (Qiagen) was used in gradually increasing amounts in different reactions depicted in FIG. 12B. FIG. 12C and FIG. 12D show the results of electrophoresis of products formed from two rounds of nick-ligate reactions. Segmentase was used in the reactions shown in FIG. 12C and masterase was used the reactions shown in FIG. 12D.

DETAILED DESCRIPTION

I. Overview

Described herein are "nick-ligate" or "nick-ligation" single tube LFR methods for preparing sequencing libraries. The methods introduce single-stranded breaks (e.g., nicks or gaps) in double-stranded target nucleic acids with controlled speed, frequency, or both. The methods also ligate adapter(s) to the 3' (3-prime) side of the break, the 5' (5-prime) side of the break, or both sides of the nicks or gaps, as further described below. Addition of one or more adapters produces an "adaptered fragment." Enzymatic reactions involved in preparing the library, e.g., nicking and ligating, can be performed in one single mixture to produce libraries of target nucleic acids with desired adapters and barcodes.

The nick-ligate methods have certain advantages that are particularly suitable for de novo assembly of sequence reads for large genomic fragment sequencing.

First, the process creates overlapping single-stranded nucleic acid fragments that remain associated with each other during the entire process of library preparation. As compared to methods (e.g., transposon insertion-based methods) that create a double-strand break at the DNA strand break sites, the methods disclosed herein avoid material loss and increase the clone coverage of target nucleic acids.

Second, as compared to the transposon-mediated co-barcoding methods (e.g., as described in Zhang et al., Nature Biotechnology, June 2017, doi 10.1038/nbt.3897) the nick-ligate methods avoid the bias caused by transposase preference for certain DNA sequences.

Third, unlike multi-step transposon-based co-barcoding methods, the library preparation and co-barcoding processes disclosed herein can be carried out as single-step, single-tube preparation.

Fourth, the size of the adaptered fragments created by the methods disclosed herein can be controlled by controlling the components in the reaction regardless of target nucleic acid. The size of the target nucleic acid fragments produced by other existing transposon-based methods is affected by the amount of high molecular weight genomic DNA in the reaction, and thus often difficult to control. In contrast, in the methods disclosed herein, size can be controlled by, e.g., balancing the amount of nicking agents and ligases.

Figure 1:
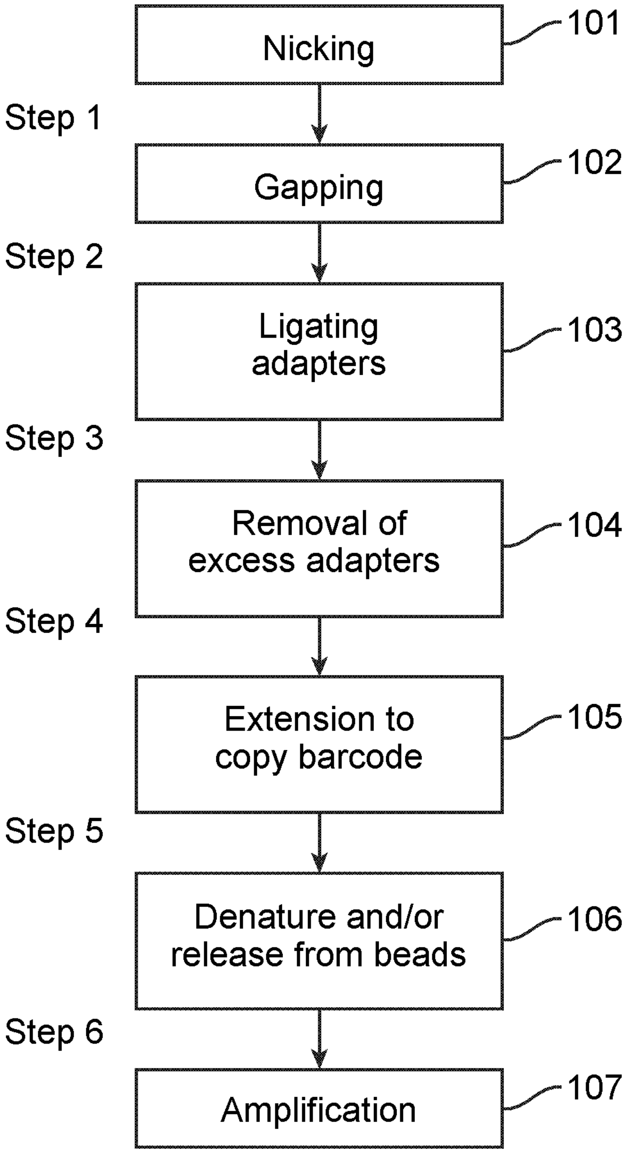
FIG. 1 shows an exemplary work flow of a library preparation method.
Figure 2:
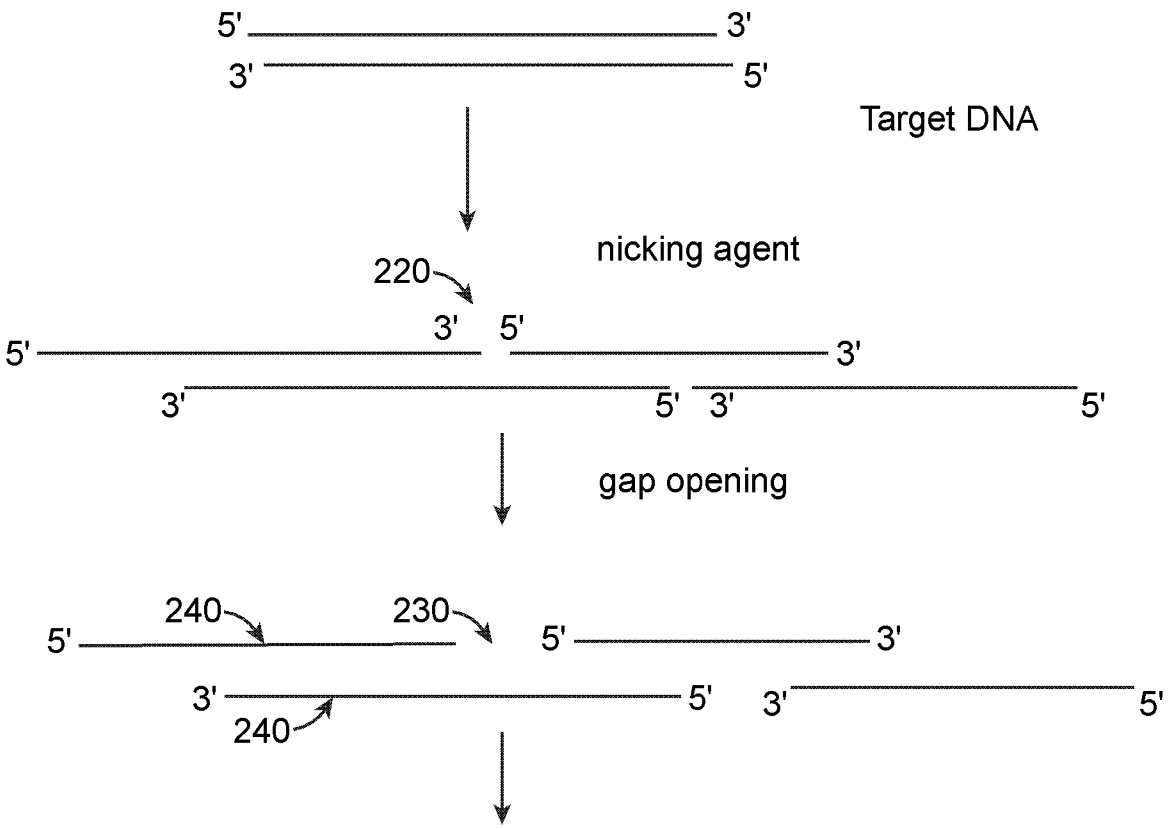
FIG. 2 illustrates nicking a double-stranded target nucleic acid (210) to generate staggered single-stranded breaks (220).

An exemplary workflow is shown in FIG. 1. In Steps 1 and 2 a double-stranded nucleic acid is nicked to produce staggered single-stranded breaks (220). In Step 3, the breaks are extended (equivalently, "widened" or "gap opened") by "gapping enzymes" such as the Klenow fragment (in the absence of nucleotides). As illustrated in FIG. 2, these nicking and gapping processes produce single-stranded gaps and overlapping nucleic acid fragments (240) ("fragments"). A portion of each of these fragments remains hybridized to a portion of another fragment having a complementary sequence.

In Step 3, the fragments are ligated to adapters. One of the adapters may be a branch ligation adapter immobilized on a bead, referred to as bead-linked branch ligation adapter or B-BLA. The other adapter may be an L-adapter that is provided in solution. Optionally, excess adapters (i.e., adapters that are not ligated to any of the fragments) may be removed by nucleases (Step 4).

In Step 5, in some cases, adaptered fragments are widened to produce double-stranded fragments that include the barcode sequence. Although disclosed herein as separate steps, the nicking and ligating can occur in a single reaction and may occur simultaneously. In some embodiments, the nicking and ligation reaction may last at least 30 minutes, e.g., at least 60 minutes, at least 90 minutes, or at least 120+ minutes. In some embodiments, the double-stranded fragments are denatured to form single-stranded molecules.

In Step 6, the denatured nucleic acid fragments are amplified, e.g., by PCR using primers annealed to the adapter sequences at both ends of the fragment. Alternatively, the denatured nucleic acid fragments can be circularized and amplified.

Variations of this workflow are also encompassed by the disclosure. Exemplary variations are shown in FIGS. 3-8.

II. Definitions

Components or a reaction in "a single reaction mixture," means that the reaction occurs in a single mixture without compartmentalization into separate tubes, vessels, aliquots, wells, chambers, or droplets during tagging steps. Components can be added simultaneously or in any order to make the single reaction mixture.

The term "staggered single-stranded breaks" refers to breaks (produced by nicking or gapping) introduced into single strands of a double-stranded or partially double-stranded DNA molecule, resulting in a plurality of overlapping single-stranded nucleic acid fragments hybridized to other single-stranded nucleic acid fragments For at least some of the nucleic acid fragments, a portion of the 5' sequence is complementary to at least a portion of the 5' sequence of another nucleic acid fragment and at least a portion of the 3' sequence is complementary to at least a portion of the 3' sequence of yet another nucleic acid fragment such that under hybridization conditions a plurality of nucleic acid fragments hybridize to each other to form a nucleic acid complex. For illustration and not limitation, a nucleic acid complex comprising four nucleic acid fragments separated by staggered single-stranded breaks is illustrated in FIG. 2. It will be appreciated that a nucleic acid complex (or "complex") may, and typically does, comprise more than four nucleic acid fragments.

The term "partially double-stranded" refers to two DNA strands that are hybridized to each other and at least a portion of one strand is not hybridized the other strand. The two DNA strands of a partially double-stranded DNA may be of different length or may be of the same length.

As used herein, "unique molecular identifier" (UMI) refers to sequences of nucleotides present in DNA molecules that may be used to distinguish individual DNA molecules from one another. See, e.g., Kivioja, Nature Methods 9, 72-74 (2012). UMIs may be sequenced along with the DNA sequences with which they are associated to identify sequence reads that are from the same source nucleic acid. The term "UMI" is used herein to refer to both the nucleotide sequence of the UMI and the physical nucleotides, as will be apparent from context. UMIs may be random, pseudo-random or partially random, or nonrandom nucleotide sequences that are inserted into adapters or otherwise incorporated in source nucleic acid (e.g, DNA) molecules to be sequenced. In some implementations, each UMI is expected to uniquely identify any given source DNA molecule present in a sample.

As used herein, the term "single tube LFR" or "stLFR" refers to the process described in, e.g., US patent publication 2014/0323316 and Wang et al., Genome Research, 29: 798-808 (2019), the entire content of which is hereby incorporated by reference in its entirety, in which, inter alia, multiple copies of the same, unique barcode sequence (or "tag") are associated with individual long nucleic acid fragments. In one embodiment of single tube LFR, the long nucleic acid fragment is labeled with "insertion oligonucleotides" at regular intervals. In one embodiment, the insertion oligonucleotides are introduced into the long nucleic acid molecule by one or more enzymes, e.g., transposases, nickases, and ligases. The barcode sequences among different long nucleic acid fragments are different. Thus, the process of labeling individual long nucleic acid fragments can be conveniently performed in, e.g., a single vessel, without compartmentalization. This process allows analysis of a large number of individual DNA fragments without the need to separate fragments into separate tubes, vessels, aliquots, wells, or droplets during tagging steps.

As used herein, a "unique" barcode refers to a nucleotide sequence that is associated with, and can be used to distinguish, individual beads. In a population of beads each having a unique barcode, the barcode sequence associated with one bead is different from barcode sequences of at least 90% of the beads in the population, more often at least 99% of the beads in the population, even more often at least 99.5% of the beads in the population, and most often at least 99.9% of the beads in the population.

The term "join," used in connection with a polynucleotide and a substrate (for example, a bead), refers to that the polynucleotide (or one terminus of the polynucleotide) directly contacts or is covalently linked to the substrate. For example, a surface may have reactive functionalities that react with functionalities on the polynucleotide molecules to form a covalent linkage. As one illustrative example, a b-BLA is immobilized on a bead via joining either the barcode oligonucleotide or the hybridization oligonucleotide to the bead.

The term "in solution," when used to in connection with an adapter (or any other polynucleotide or polynucleotide complex) used in the methods or compositions disclosed herein, refers to that the adapter (or any other polynucleotide or polynucleotide complex) is not immobilized on a substrate and can freely move in solution. When use to describe a reaction, as in "a reaction performed in solution" refers to that the reaction occurred between nucleic acids, all of which are in solution.

The term "adapter" is used herein in different senses, as will be apparent from context. In some embodiments, "adapter" refers to a "branch ligation adapter (BLA)" as discussed below. In some embodiments, "adapter" refers to an "L-adapter" as discussed below. A BLA that is immobilized on a bead is referred to as a bead-linked branch ligation adapter ("b-BLA"). A BLA that is in solution is referred to as solution branch ligation adapter ("s-BLA")

The term "adaptered nucleic acid fragment," refers to a polynucleotide comprising one target nucleic acid fragment and one or more adapter sequences. For example, the one or more adapter sequence may be a sequence in the b-BLA or a sequence in an L-adapter, or both.

The term "excess adapter," (e.g., an excess b-BLA adapter) or "unlighted adapter" refers to an adapter that is immobilized on the bead but is not ligated to a target nucleic acid fragment despite being in a condition where other bead adapter is ligated to a target nucleic acid fragment.

The term "extended nucleic acid fragment," or "barcoded extension product," refers to the fragment ligated to the adapters and have extended to include a copy of the barcode.

The term "ligated product," or "ligated adapter" refers to the product comprising a target nucleic acid fragment and at least an adapter sequence from the b-BLA adapter. In some cases, the ligated product may further comprise an adapter sequence from the b-BLA at one end and an adapter sequence from another adapter (e.g., the L-adapter) at the other end.

The term "ligated first adapter," refers to the product formed by ligation of a target nucleic acid fragment and a sequence of the first adapter.

The term "adapter sequence," refers to a sequence on either strand of an adapter as will be clear from context. That is, "adapter sequence," can refer to both the sequence of an adapter on one strand and the complementary sequence on the second strand. For example, a b-BLA adapter sequence can be a sequence on the barcode oligonucleotide or a sequence on the hybridization oligonucleotide.

The term "branch ligation adapter," "Branch adapter" or "BLA," refers to a partially double-stranded adapter. Said partially double-stranded adapter comprises (i) a double-stranded blunt end comprising a 5' terminus of one strand and a 3' terminus of the complementary strand and (ii) a single-stranded region comprising a barcode sequence. The 5' terminus of the double-stranded region of the branch adapter can be ligated to the 3' terminus of the nucleic acid fragment via branch ligation as further described below.

The term "bead-immobilized branch ligation adapter," or "b-BLA" refers to a branch ligation adapter immobilized on a bead. A b-BLA disclosed herein comprises a barcode oligonucleotide and a hybridization oligonucleotide, which are hybyridized to each other.

The term "barcode oligonucleotide," refers to the strand of the b-BLA that comprises a barcode sequence.

The term "hybridization oligonucleotide," refers to the strand of the branch ligation adapter that is complementary to the barcode oligonucleotide.

The term "reversible terminator nucleotide," or "reversible terminator," refers to a nucleotide having a 3' reversible blocking group. "Reversible blocking group" refers to a group that can be cleaved to provide a hydroxyl group at the 3'-position of the nucleotide that can be ligated to the 5' phosphate group of another nucleotide. The reversible blocking group can be cleavable by an enzyme, a chemical reaction, heat, and/or light. Exemplary nucleotides having 3' reversible blocking groups are known in the art and disclosed in U.S. Pat. No. 10,988,501, the relevant disclosure is herein incorporated by reference.

The term "copy" refers to generating a complementary nucleotide strand of a template by primer extension.

III. Exemplary Embodiments of the Methods

The nick-ligate method can be carried out according to various schemes. This section provides exemplary embodiments of the methods. A practitioner with skill in the arts of molecular biology and sequencing guided by this disclosure will recognize numerous variations of individual steps and reagents can be incorporated into the schemes below.

Methods

1. Nicking

In one approach, the target nucleic acids are combined with one or more nicking agents, which create staggered single-stranded breaks in double-stranded DNA. In some embodiments, the nicking agent is an enzyme (generally referred to as a 'nickase'), e.g., an endonuclease that cleaves a phosphodiester bond within a polynucleotide chain or removes one or more adjacent nucleotides from the polynucleotide chain. In some cases, the nickase is a non-sequence specific endonuclease, which nicks a DNA strand at random positions. Non-limiting examples of nicking agents include *vibrio vulnificus* nuclease (Vvn), Shrimp dsDNA specific endonuclease, DNAse I, segmentase (MGI), and masterase (Qiagen). In some embodiments, the nicking agent is a site- or sequence-specific nuclease such as a restriction endonuclease, that nicks DNA at its recognition sequence. Non-limiting examples of site-specific nickases include Nt.CviPII (CCD), Nt.BspQI, and Nt.BbvCI, as described in Shuang-yong Xu, BioMol Concepts 2015; 6(4): 253-267, the entire disclosure is herein incorporated by reference.

In some embodiments nicking agents disclosed herein can also be chemical nicking agents. Non-limiting examples of the chemical nicking agents include dipeptide seryl-histidine (Ser-His), $Fe2+/H_2O_2$, or $Cu(II)$ complexes/$H_2O_2$.

Thus, nicking agents can be grouped into categories such as non-specific nickase, site-specific nickases, or chemical nicking agents. In some embodiments, the method uses two or more nicking agents. In some embodiments the method used two or more nicking agents from the same category of nicking agents. In some embodiments, the method uses nicking agents from different categories.

A number of parameters can affect the length of the nucleic acid fragments separated by the breaks. Typically, the higher the concentration of the nicking agent, the longer treatment time by the nicking agents, the shorter the length the fragments. By adjusting one or more of these parameters, the length of the fragments can be controlled within a desired range. In some embodiments, the average length of the nucleic acid fragments resulted from the nicking is between 200 and 10000 nucleotides, e.g., 200-500 nucleotides or 400-1000 nucleotides or 1000-10000 nucleotides.

2. Gapping

In some embodiments, nicks created by the nickase are extended (widened) by an exonuclease to form gaps. This process can be referred to as "gapping" and the exonucleases used in process can be referred to as "gapping enzymes." Examples of enzymes with 3' exonuclease activity include DNA Polymerase I, Klenow Fragment (in the absence of nucleotides), Exonuclease III, and others known in the art. Examples of enzymes with 5' exonuclease activity include Bst DNA polymerase, T7 exonuclease, Exonuclease VIII truncated, Lambda exonuclease, T5 exonuclease, and other exonucleases known in the art. Low processivity exonucleases (i.e., exonucleases that remove nucleotides from the end of a polynucleotide at a relatively low rate) are preferred to open a short gap (e.g. 2-7 bases, 3-10 bases, or 3-20 bases) and disassociate from DNA to allow adapter ligation. In the case where an exonuclease is used, if necessary, protection of the DNA adapters from exonuclease digestion can be achieved by introducing phosphorothioated bonds between bases (or modified bases) at the 5' and 3' ends of the adapters.

FIG. 2 illustrates a process of using one or more nicking agents and one or more gapping enzymes to generate overlapping nucleic acid fragments (240), separated by staggered single-stranded breaks (230).

3. Addition of Adapters (Ligating)

As discussed above and illustrated in FIG. 2, nicking and gapping generate a plurality of fragments (240) each having a 5' terminus and a 3' terminus. In some embodiments, "fragments" are single-stranded although, as discussed above and elsewhere herein, fragments may be hybridized to complementary strands to, for example, form a nucleic acid complex. A first adapter is ligated to one terminus (which may be the 5' terminus or the 3' terminus) of fragments and a second adapter (which is different from the first adapter) is ligated to the other terminus. The result is a plurality of adaptered fragments having two different adapter sequences; and all of the adaptered fragments produced in a reaction have the same defined arrangement (e.g., first adapter sequences at 5' and second adapter sequences at 3', or, alternatively, second adapter sequences at 5' and first adapter sequences at 3').

In one aspect of the invention, the first adapter is ligated to the 3' terminus of the fragments, and a second adapter is ligated to the 5' terminus of the fragments. In some embodiments, the first adapter is a b-BLA and is ligated to the fragment in the process of "3' branch ligation". In some embodiments, the second adapter is an "L-adapter." In some embodiments, ligations of the first adapter and second adapters occur in the same reaction mixture as the nicking and gapping reactions.

First Adapter Ligation

In some embodiments, the first adapter is a BLA. BLAs are known in the art and are defined above. A BLA comprises (i) a double-stranded blunt end comprising a 5' terminus of one strand and a 3' terminus of the complementary strand and (ii) a single-stranded region comprising a barcode sequence. The double-stranded blunt end provides a 5' phosphate which can be ligated to the 3' of the target nucleic acid fragments via 3' branch ligation. 3' branch ligation involves the covalent joining of the 5' phosphate from a blunt-end adapter (donor DNA) to the 3' hydroxyl end of a duplex DNA acceptor at 3' recessed strands, gaps, or nicks. In contrast to conventional DNA ligation, 3' branch ligation does not require complimentary base pairing. 3' branch ligation is described in Wang et al., BioRxiv, Jun. 29, 2018, doi:https//doi.org/10.1101/357863; PCT Pub. No. WO 2019/217452; US Pat. Pub. US2018/0044668 and International Application WO 2016/037418, US Pat. Pub. 2018/0044667, as well as Wang et al., Jun. 29, 2018, http://dx.doi.org/10.1101/357863, all incorporated by reference for all purposes.

Using 3' branch ligation, it is theoretically possible to amplify and sequence all sub-fragments of a captured genomic molecule. Thus, 3' branch ligation has broad range of molecular applications, including, e.g., attaching adapters to DNA or RNA during NGS library preparation.

In addition, this ligation step enables a sample barcode to be placed adjacent to the genomic sequence for sampling multiplexing. The benefit of using these adapters for sample barcoding is that the barcode can be placed adjacent to the genomic DNA so that the same primer can be used to sequence the barcode and the genomic DNA and no additional sequencing primer is required to read the barcode. Sample barcoding allows preparations from multiple samples to be pooled before sequences and distinguished by the barcode. 3' branch ligation adapters can be synthesized in 96, 384, or 1536 plate format, with each well containing many copies of the adapter carrying the same barcode and each barcode being different between wells. After capture on beads these adapters can be used for ligation in 96, 384, or 1536 plate format.

3' branch ligation can be performed as a simple, low cost, bias free method for standard sequencing library preparation or in the presence of barcoded beads (attachment to beads can be on the 3' or 5' end of the barcode adapter) as a co-barcoding library preparation method. This strategy relies on a property of T4 DNA ligase, that it can ligate a double-stranded DNA adapter to a 3' end of DNA in a nick or gap so called "3' branch ligation" as described in Wang et al., DNA Research, 2019 Feb. 1 16(1): 45-53. Because this novel ligation does not require degenerate single-stranded bases on the end of the adapter to hybridize in the gap, it allows more efficient adapter ligation on beads having limited adapter binding capacity. Unlike ligation of the L-adapter, which may require a larger gap (e.g. 4-7 bases), 3' branch ligation can be performed in nicks or very small gaps (1-base gaps). Also unlike ligation of 5' degenerate L-adapter, which may require high concentrations of this 5' degenerated L-adapter to compensate for the fact that ligase cannot bind to the single-stranded 5'-phosphate end of the L-adapter before hybridization.

To enable the most efficient 3'-branch ligation on beads, these adapters may have stretches of the same base or stretches of simple repeats to improve access to the target DNA imperfectly (e.g., free loose loops) wrapped around each bead. Single-stranded binding protein (SSB) may be bound to the single-stranded portion of each adapter before mixing beads with genomic DNA.

In some embodiments, the first adapter is a b-BLA which comprises two polynucleotide strands, referred to herein as the "barcode oligonucleotide" and the "hybridization oligonucleotide." The barcode oligonucleotide is longer than the hybridization oligonucleotide and comprises at least one barcode. The barcode oligonucleotide is hybridized to the hybridization oligonucleotide to form a complex that is partially double-stranded and has a blunt end.

In some embodiments, the barcode oligonucleotide has a 5' phosphate that can be ligated to the 3' terminus of a 3' recessed fragment in a branch ligation, and has a 3' terminus that is joined to a bead; while the hybridization oligonucleotide is not joined to the bead, and the hybridization oligonucleotide a 3' blocker nucleotide (e.g. a dideoxy blocker nucleotide) that prevents formation of a phosphodiester bond and thus prevent self-ligation of the branch adapters. The 3' branch ligation results in the barcode oligonucleotide ligated to the fragment. See FIG. 9A.

In some embodiments, the hybridization oligonucleotide has a 5' phosphate that can be ligated to the 3' of a 3' recessed fragment in a branch ligation and has a 3' terminus that is joined to a bead; while the barcode oligonucleotide is not joined to the bead, and the barcode oligonucleotide has a 3' blocker nucleotide that prevents formation of a phosphodiester bond. The 3' branch ligation (discussed below) results in the hybridization oligonucleotide ligated to the fragment See FIG. 3 and FIG. 4.

In some embodiments, the first adapters are in solution. In some embodiments, some of the first adapters are immobilized on the beads and some of the first adapters are in solution.

Second Adapter Ligation

The fragments in the nicked and gapped DNA (that are associated with each other) are ligated to a second adapter. The second adaptor may be an L-adaptor, an s-BLA, or any double-stranded or partially double stranded adapter.

In some embodiments, the second adapter is an L-adapter. In some embodiments, the L-adapters are in solution. L-adapters are described in U.S. Pat. No. 10,479,991, the entire disclosure of which is herein incorporated by reference. L-adapters used in the present method are single-stranded adapter comprising a hybridization region and a tail region. The hybridization region of the L-adapter comprises degenerate bases at the 3' end, e.g., 1-10, e.g., 3-8, or 4-7 degenerate nucleotides (Ns) at the 3' end. Thus allows the L-adapter to hybridize to a variety of target sequences. When contacted with the nucleic acid fragments in the nicked and gapped DNA described above, the hybridization region of the L-adapter anneals to the complementary sequence in the target nucleic acid, while the tail region remains single-stranded. Under ligation-permissible conditions, the 3' end of the L-adapter is ligated to the 5' end of the nucleic acid fragment. See e.g., FIG. 3-5.

In some embodiments, the L-adapter comprises specific bases next to the hybridization region to improve the ligation efficiency and the reduction of artifacts. For example, if the nickase used in the reaction preferentially cuts at certain bases or sequences, the same bases (or complementary bases) can be engineered to the end of the L-adapter to increase ligation efficiency. In some embodiments, two or more L-adapters having different sequences, e.g., having different number of degenerate nucleotides can be used in the same reaction.

In some embodiments, the second adapters are partially stranded adapters (FIGS. 6, 7B, and 8). In some embodiments, the second adapters have double-stranded blunt ends. In some embodiments, after the fragments in the nicked and gapped DNA are ligated to the first adapter and formed double-stranded DNA via primer extension, the second adapters can be ligated to the terminus that is opposite from the first adapter. See FIGS. 5, 6B, and 7. In some embodiments, the second adapter is joined to a fragment by a blunt end ligation. In some embodiments, the second adapter is joined to a fragment by a single base overhang ligation provided that a polymerase was used during the extension step that leaves an A tail.

Ligation of Two Adapters to the 5' and 3' Side of Nicks or Gaps in the Same Reaction In some embodiments, the first adapter (e.g., a b-BLA) can be added to the 3' terminus of the fragment, and the second adapter (e.g., an L-adapter) can be ligated to 5' terminus of the fragments of the nicked and gapped DNA. And the ligations are performed in the same mixture while nicking and gapping also occur. In some embodiments, after one round of nick-ligate reaction, the beads wrapped with the genomic DNA can be incubated with nickase and/or gapping enzymes, in the presence of additional first and/or the second adapters, so that a second round of nick-ligate reaction occurs. This nick-ligate process can be repeated for multiple rounds, for example two rounds, three rounds or four rounds to improve the yield of the products ligated with two adapters. Illustrative examples are shown in Examples 6 and 7.

Conditions can be optimized for simultaneous ligation of both adapters in the nick by adjusting the concentration of L-adapters, temperature, cycling, pH, salt concentration, other additives to enhance DNA breathing of the 3' end with branch-adapter that has been ligated to the genomic fragments, which allows a short single-stranded region for L-adapter hybridization and ligation. See section 5 below, "Conditions for simultaneous nicking and ligating". In some embodiments, to achieve more complete ligation and thus more non-duplicated read coverage, additional branch ligation adapters can be added in solution (s-BLAs) to the reaction, in addition to the b-BLAs.

In some embodiments, an enzyme with 5' exonuclease activity is added to the reaction to remove excess first adapters. This can be performed before the L-adapter ligation or simultaneously with the L-adapter ligation. Because excess adapter must be removed, a higher concentration of L-adapter, e.g., in a range from 0.01 to 100 μM, from 0.1 to 50 μM, from 0.5 to 30 μM, from 1 to 20 μM, maybe used without generating a substantial amount of the bead-adapter+L-adapter ligation artifact. Adaptered fragments having both the first adapter sequence and the second adapter sequence (e.g., the L-adapter) can be sequenced on Illumina type and other systems that do not require circularization. Aspects of sequencing are further described below.

In some cases, an additional enzyme with 3' exonuclease activity (such as DNA Polymerase I, Klenow Fragment without nucleotides, Exonuclease III, or the like) or with 5' exonuclease activity (Bst DNA polymerase full length or Taq polymerase without nucleotides, T7 exonuclease, Exonuclease VIII truncated, Lambda exonuclease, T5 exonuclease, or similar) can be added as well to increase the opening of the nick for more room for ligation of the second adapter (e.g., the L-adapter). Enzymes or combinations of enzymes with both 3' and 5' exonuclease activity have an advantage to make a gap for L-adapter ligation even if the branch adapter ligates in the nick. In the case where an exonuclease is used, if necessary, protection of the DNA adapters can be achieved through phosphorothioated bonds between bases and/or modified bases at the 5' and 3' ends of the adapters. As discussed above, this reaction can be performed in the presence of polyethylene glycol or betaine to increase the activity of ligation and/or the nickase enzyme.

At this point, excess adapters can be removed as discussed above, if needed. A low concentration of L-adapter and other conditions may be used to reduce adapter-adapter ligation (e.g., the ligation between the L-adapter itself or the ligation between the b-BLA and the L-adapter) and skip excess adapter removal by exonucleases. Otherwise, PCR can now be performed as both sides of the sub fragments now have adapter sequences. After PCR is performed or if PCR was skipped for a PCR-free version of the process, then circularization followed by rolling circle amplification is the next step as described in the previous section.

In one illustrative embodiment, in a single reaction mixture, a non-specific nicking nuclease, a DNA ligase, and a first adapter, a second adapter are mixed with the double-stranded target nucleic acids to produce fragments having adapter sequences at both termini. In preferred embodiments, one of the first and the second adapter is bound to a micron sized bead and the other adapter is in solution.

The process of adding two adapters in a single reaction mixture can be performed in solution as a simple, low cost, bias free method for standard sequencing library preparation. This process can also be used as a co-barcoding library preparation method when used with barcoded beads with adapters attached thereon.

4. Conditions for Simultaneous Nicking and Ligating

In some embodiments, nicking and gapping the target nucleic acid and ligating one or more adapters to the fragments produced by the nicking and gapping can be performed in the presence of additives (e.g., polyethylene glycol or betaine) to increase the activity of ligase, the activity of the nicking agents, or both. In some embodiments, ligating comprises ligating at least the bead-bound first adapter (e.g., b-BLA) to the nucleic acid fragment. In some embodiments the ligating includes ligating both the bead-bound first adapter and the second adapter (e.g., the L-adapter) in solution to the nucleic acid fragment.

4.1 Temperature

The reaction may be maintained at a temperature within a range from 5-65° C., e.g., 5-42° C., 10-37° C., or 5-15° C. In some embodiments, the reaction is maintained at room temperature, 37° C. In some embodiments when a thermostabile ligase and nicking enzyme are used, the reaction may be kept at a temperature that is higher than 37° C. In some embodiments, the reaction is subjected to a condition cycling between a lower temperature (5° C.-25° C., for example, 10° C.-15° C.) and a higher temperature (e.g., 37° C. or higher) for multiple cycles (e.g., 5-100 cycles, or 20-60 cycles, 30-55 cycles, etc.). Illustrative examples are shown in Examples 1-7.

4.2 pH

In some embodiments, the pH of the reaction mixture is maintained at a pH within a range from 5.0 to 9.0, e.g., from 7.0 to 9.0, to accommodate all enzymatic functions required for the library preparation. The duration of the nicking and ligating reaction may vary depending on the desired size of the nucleic acid fragments and other conditions, e.g., enzyme (including polymerase, exonuclease, or both) concentration, time, temperature, amount of input DNA.

4.3 Time

Typically the duration of the nicking and ligating reaction may last from 5 minutes to 5 hours, e.g., 15-90 minutes, or 30-120 minutes. The reaction may be terminated using methods well known in the art. In some embodiments, the nicking and ligating are performed in solution, and the reaction can be terminated through a DNA purification method (such as Ampure XP beads, from Beckman Coulter). In some embodiments, the nicking and ligating are performed on beads, and the reaction can be terminated by washing the beads with a buffer (e.g., a Tris NaCl buffer) to remove the enzymes and components required for the nicking and ligating reactions.

4.4 Enzyme

The methods and compositions described herein the allows nicking and ligating to occur in a single reaction mixture. In some embodiments, the conditions and enzymes are selected so that ligating occurs at a higher rate than nicking/gapping. This assures fraction of nicks that are initially gapped will get adapter ligated to most of them before subsequent gappings, thus minimizing DNA loss. The methods and composition disclosed herein allows for a high nick-resealing rate, e.g., 70-100% nick-resealing rate, e.g., 70-90%, 80-90%, 80-95%, 90-99%). A nick-resealing rate disclosed herein refers to that the percentages of gaps being opened are resealed by the ligase. The high nick-resealing rate may be achieved by a number of ways. In some embodiments, the nicking is performed using a low activity nickases. In some embodiments, the nicking is performed using a nickase at a low concentration, e.g., 0000001-10 U/ul. In some embodiments, the ligating is performed using a ligase having a high ligating rate. In some embodiments, the ligating is performed using a ligase at a high concentration, e.g., 1-100 U/ul.

4.5 Order of Adding Components

The order of adding components the single reaction mixture may vary. In some embodiments, ligase is added prior to adding nickase or simultaneously with adding the nickase. The order of adding ligase and loading target nucleic acids to beads may vary. In some embodiments, the ligase is added to the beads immobilized with adapters before adding target nucleic acids (e.g., genomic DNA). In some embodiments, target nucleic acids are loaded to the beads before adding ligase.

In some embodiments, it is desirable to load target nucleic acid onto the beads before adding any of the nickase, ligase so that the target nucleic acid are bound to the beads before nicking and ligating. Genomic DNA typically can wraps very fast around micron sized paramagnetic beads, typically about 1-10 minutes. In some embodiments, additional procedures can be taken to increase the binding efficiency of target nucleic acid to the beads, which may be particular useful for binding long DNA (e.g., those longer than 200 kb) to large beads (e.g., beads having a diameter of 3 micron or greater). In some embodiments, the target nucleic acid is bound to beads in a buffer comprising PEG had relatively high concentration, e.g. 3-12%, e.g., 5-10%, and a higher PEG concentration generally resulting higher binding. In some embodiments, the target nucleic acid is bound to beads in a buffer having relatively high pH to enhance the absorption of target nucleic acids to the beads. In some embodiments, the pH is greater than 7.5, e.g., 7.5-9, 8.0-9.0, or 8.0-8.5. The high pH increases DNA adsorption especially in buffers having lower PEG concentration, e.g., 5%. In some embodiments, the buffer comprises a low salt concentration, e.g., 10 mM $MgCl_2$. The methods and compositions disclosed herein allows, long DNA wraps around beads in these conditions quickly (e.g., 5-15 minutes with most of DNA bound in 1-5 or 2-10 minutes) minimizing fragmentation of long DNA (e.g., >200 kb, or >300 kb or >500 kb) before binding to beads. In one example, gDNA having the length of over 1 Mb can bind a bead having a diameter of about 3 μm.

Target nucleic acids that are bound to the beads can remain accessible to enzymatic reactions like nicking, gapping, or adapter ligation. This allows co-barcoding of a long DNA fragments (e.g., 20-500 kb) bound to a bead at 10-1000 contact points. This allows for a general protocol of multiple consecutive enzymatic reactions on the bead-adsorbed DNA, especially in conditions that maintain DNA binding to beads as described above.

DNA may be released from beads in preparation for sequencing. Methods of releasing DNA include but not limited to using low salt buffer (<200 mM) with pH in the range of 7 to 8, e.g., about 7.5 in between 10 minutes and 1 hour, e.g., about 15 minutes to about 45 minutes, about 15 minutes to about 45 minutes, or about 30 minutes.

5. Optional Step of Removal of Excess Bead-Bound Adapters

Optionally, after nicking and ligating, various enzymes are used to remove excess adapters, i.e., adapters that are not ligated with target nucleic acid fragments. In some embodiments, the bead-bound adapters are partially double-stranded, each of which comprises a relatively short double-stranded region (e.g., between 6 and 20 bases) and can be denatured relatively easily. That is, the adapters can be denatured to single-stranded DNA under conditions that will not result in disrupting the double-stranded genomic DNA immobilized onto the beads. This can most easily be achieved by increasing the temperature to the melting point of the short double-stranded region.

Table 1 shows various enzyme that may be used for this purposes.

TABLE 1

Exemplary enzymes that may be used to remove excess bead-bound adapters

| Type of DNA substrate | Direction of degradation | exonuclease |
|---|---|---|
| Single-strand | 5'-->3' | RecJ Exo VII |
| Single-strand | 3'-->5' | Exo I, ExoT |
| Double-strand | 5'-->3' | Bst polymerase, Taq polymerase, T7 exonuclease, Exonuclease VIII truncated, Lambda exonuclease, T5 exonculease, |
| Double-stranded | 3'-->5' | ExoIII, T4 DNA polymerase or Phi29 DNA polymerase, DNA Polymerase I, Klenow Fragment without nucleotides, Exo III |

The denatured, single-stranded, bead-bound adapters can then be removed by using exonucleases. In some embodiments, excess bead-bound adapters that have 3' termini attached to the beads are removed using an exonuclease (e.g., RecJ or ExoVII) that can remove nucleotides from single-stranded DNA in the 5' to 3' direction. In some embodiments, excess bead-bound adapters that have 5' termini joined to the beads are removed using an exonuclease (e.g., Exo1, ExoT) that can remove nucleotides from single-stranded DNA in the 3' to 5' direction.

Alternately, no denaturation is required and the excess, partially double-stranded bead-bound adapters can be digested by a mixture of single-strand specific exonucleases and an enzyme possessing 3' to 5' exonuclease activity on dsDNA, such as ExoIII, T4 DNA polymerase or Phi29 DNA polymerase in the absence of dNTPs. In this embodiment, genomic dsDNA will be protected from degradation by these enzymes by the adapter ligated to the 3' termini of the DNA nick or gap. The ligation results nucleic acid fragments having single-stranded ends, which are not substrate for these dsDNA-specific exonucleases.

In another approach, the short double-stranded region of the bead-bound adapters can be designed with specific bases (e.g., Uracil or Inosine) and these bases can be removed by treatment with the corresponding DNA glycosylases (e.g., UDG or hAAG) (to create abasic sites), and then EndoIV, EndoVIII, APE1, or any other enzyme that can remove abasic sites. Using this strategy, the melting temperature of the short double-stranded region can be further lowered as the length of contiguous double-stranded regions is further reduced after removal of these bases.

In yet another approach, if the reaction was performed in solution and excess adapters can be removed through a DNA purification method (such as Ampure XP beads). In yet another approach, when the reaction is performed on beads, the excess adapter and product ligated to adapter can be released from the beads through an enzymatic release. In some embodiments, the bead-bound adapters comprise uracils, or inosines, or both, at positions proximal to the beads, and enzymes can be added to release these bases and thus release the adapters from the beads. In some embodiments, the adapters are bound to the beads through bonds that are susceptible to a chemical treatment, and the chemical can be added to release the adapters. In one example, the adapter is bound to the bead via a biotin streptavidin interaction, heat or treating the bead-bound adapters with formamide can break the interaction. In another example, the adapter is bound to the bead via a photocleavable linker and light can be used to cleave the linker and release the adapter from the bead.

In some embodiments, the method does not include a step to remove the excess bead-bound adapters; and after nicking and ligating steps as described above the primer extension step is performed. In some embodiments, the primer extension step is performed after the removal of the excess bead-bound adapters.

6. Extension to Copy the Barcode

In some embodiments, the nucleic acid fragment ligated with the branch adapter is then extended by a DNA polymerase to copy the barcode. One illustrative embodiment is shown in FIG. 6.

Figure 3A:
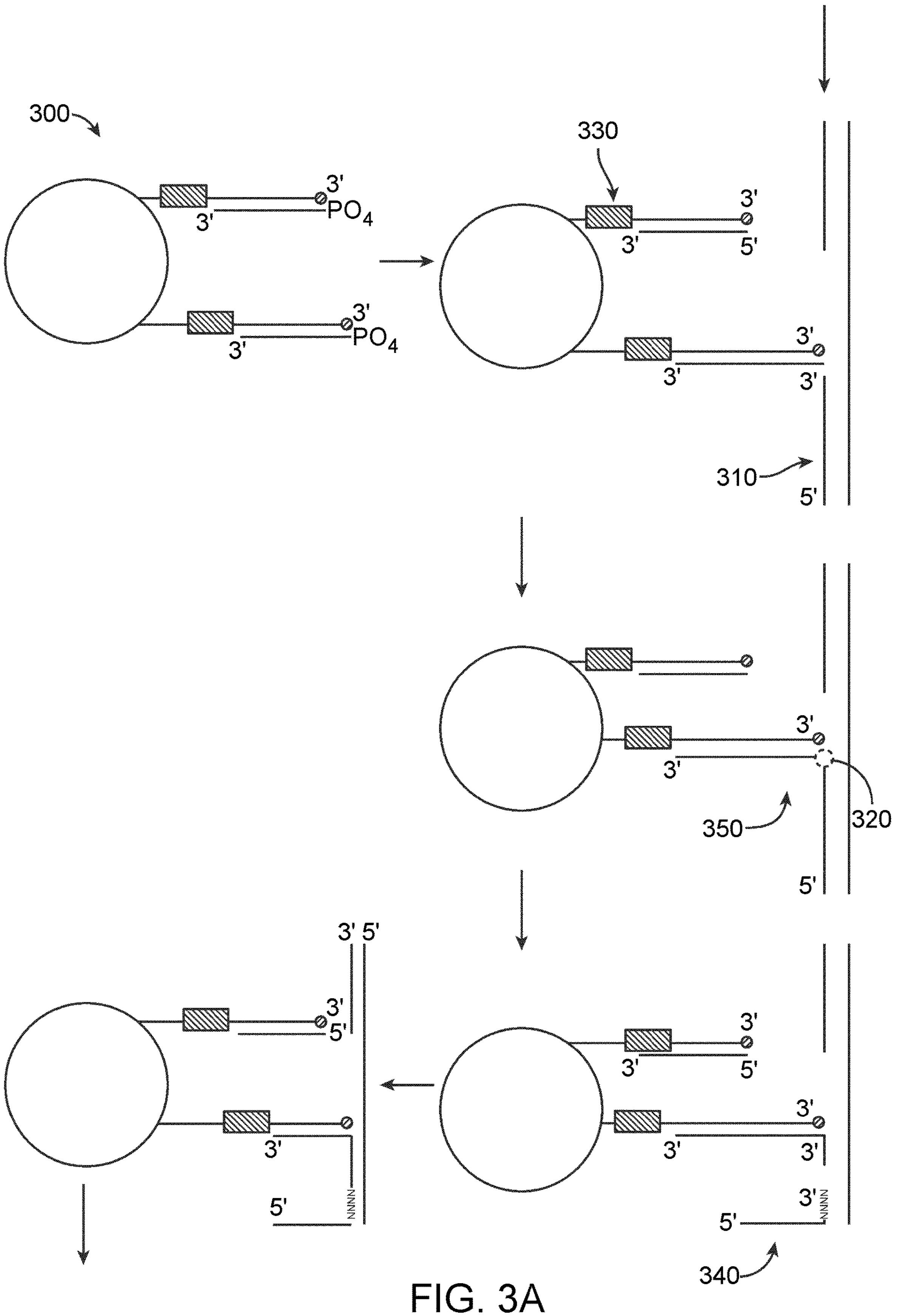
FIGS. 3A and 3B shows an exemplary method of adding a b-BLA adapter (320) to the 3' end of the target DNA (310) through branch ligation (320) and adding an L-adapter (340) to the 5' end of the target DNA in one single reaction mixture.
Figure 3B:
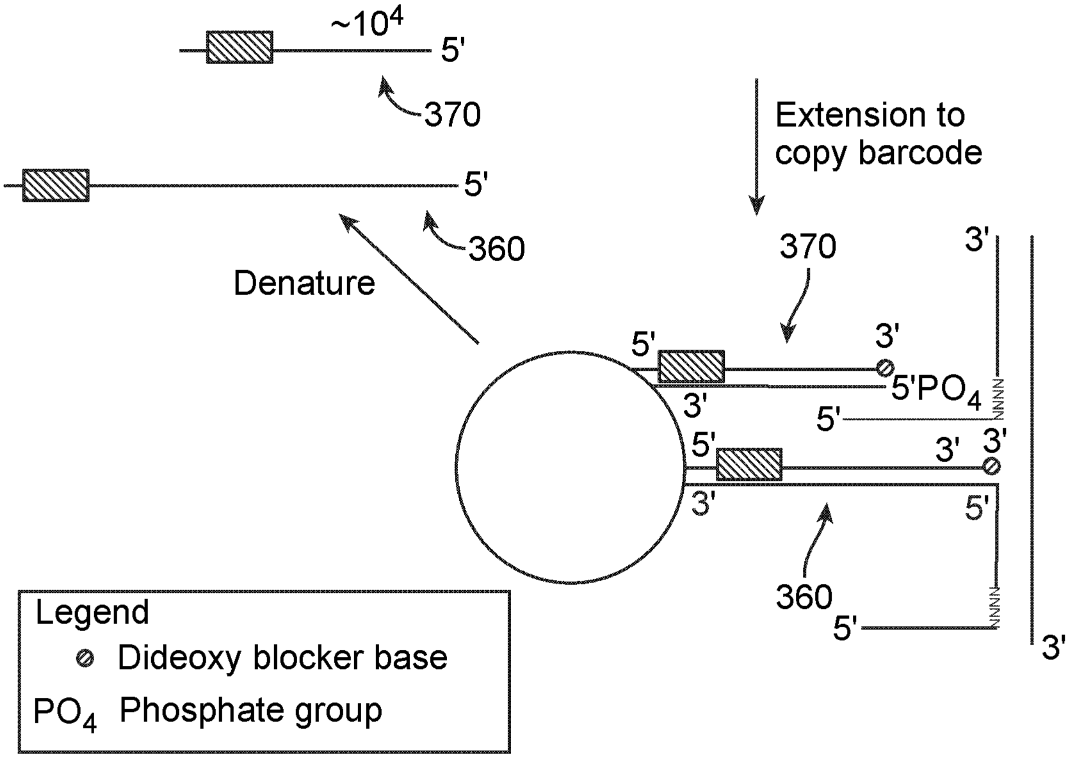

In some embodiments, a primer extension step can be performed either on the beads or in solution to copy the barcode. In some embodiments, a denature step (e.g., by heat) is performed to produce single-stranded fragments ligated with adapters, and a polymerase without strand displacement activity (such as pfu, pfuCx, Taq polymerase, DNA pol 1) is used to extend the strand that is ligated with the nucleic acid fragment to copy the barcode. FIG. 3 and FIG. 4. In some embodiments, no denaturing step is performed and the primer is extended using a strand displacing polymerase (e.g., phi29 polymerase or Bst). In one illustrative example, the reaction is denatured at a 95° C. for 3 minutes, which is followed by annealing a primer at 55° C. for 3 minutes, and extending the primer at 72° C. for 10 minutes using pfuCx.

In some embodiments, another round of purification can be performed at this step if the barcoded extension product is in solution. If still bound to beads, the beads can be washed in Tris NaCl buffer.

In scenarios where the extended nucleic acid fragments already contains two adapters, one to each terminus of the nucleic acid fragment, as shown in FIGS. 3 and 4, the extended fragments can be released from the beads for further processing as described below. In some embodiments, only one adapter is in the extension product, such as shown in FIGS. 6 and 7A, a ligation of the second adapter to the opposite terminus of the nucleic acid fragment from the first adapter can be performed. In some embodiments, the second adapter is ligated to the nucleic acid fragments by a blunt end ligation. In some embodiments, where a polymerase was used during the extension step that leaves an A tail, the second adapter can be ligated to the nucleic acid fragments by a single base overhang ligation. Importantly, for the purpose of doing this in a PCR-free manner, 3' OH of the adapter is ligated to the 5' PO4 of the product. This is the original DNA strand (not the copy made during extension). For PCR based library prep strategies, another round of DNA purification is typically performed at this point and followed by PCR amplification.

7. Controlled Extension to Separate Ligated and Unligated Adapters 7.1 Controlled Extension In another aspect, after performing branch ligation of the first adapter (e.g., a b-BLA) to the nucleic acid fragments separated by single-stranded breaks as described above, the method comprises extending a primer hybridized to the first adapter sequence under conditions that permits controlling of the extent of the extension reaction. These extension-controlling conditions include but are not limited to, selecting a polymerase(s) with a suitable polymerization rate or other properties, and by using a variety of reaction parameters including (but not limited to) reaction temperature, duration of the reaction, primer composition, DNA polymerase, primer and nucleotide concentration, additives, and buffer composition. In some cases, the extension can be controlled by a mixture of reversible terminators and normal nucleotides for the extension. The ratio of the amount of reversible terminator nucleotides to the amount of normal nucleotides can be adjusted to achieve the extent of the extension; in general, a higher ratio of the amount of reversible terminator nucleotides to the amount of normal nucleotides will result in a less complete extension. In some embodiments, the extension is controlled such that it only adds about 100-150 bases.

In some embodiments, the primer hybridizes to a sequence that is 3' to the barcode sequence in the first adapter and is extended under the extension-controlling conditions. Under these conditions extension of the primer to copy the ligation product—produced by ligating a first adapter to a target fragment—is incomplete, resulting a partially double-stranded molecule; while extension of the primer to copy the unligated b-BLA is complete, resulting a double-stranded molecule. Illustrative example of using controlled extension to prepare adaptered nucleic acid fragments are shown in FIGS. 10A-10B and FIGS. 11A-11B.

The incomplete extension of the primer to copy the ligated first adapter would leave a 5' overhang that can be used for 3' branch ligation. If reversible terminators are used, at the end of the extension reaction, blocking groups of the reversible terminators are removed to restore the 3' OH group. At this point 3' branch ligation can be performed to ligate a second adapter to the 3' terminus of the fragment, thus producing an adaptered fragments having a first adapter sequence at one terminus and a second adapter sequence at the other terminus. In some embodiments the reversible terminators can be added at different concentrations, at different time points, or different cycles to provide overlapping coverage across most nucleotides in the nucleic acid fragments.

The complete extension of the primer to copy the unligated first adapter results a double-stranded molecule, which can be degraded and removed by enzymes having double-stranded DNA exonuclease activity, see Table 1.

7.2 Remove Excess Adapters

The following exemplary approaches can be used to remove excess unligated adapters (i.e., adapters that are not ligated to any nucleic acid fragments) to minimize the negative interference of these unligated adapters in the library preparation.

7.2.1 Remove Unligated Adapters by Bead Purification

In some embodiments, excess adapters in solution can be removed by Ampure XP bead purification (Beckman Coulter, Brea, CA).

7.2.2 Block Unligated Adapters with Hairpin Adapters

In some embodiments, the excess adapters can be degraded or blocked using methods include but not limited to the following approaches. The first method, described in FIGS. 9A and 9B, uses a controlled primer extension such that the extension only adds about 100-150 bases. The polymerase (e.g., a Tag polymerase) used in this extension does not have 3'-5' exonuclease activity and it can generate blunt ends and add an A tail at the 3' terminus. This will cause complete extension and A tailing of excess adapter (i.e., adding A to the 3' terminus of the adapter) (950), but extension of to copy adaptered fragments (940) will be incomplete. Next, ligation is performed with a hairpin adapter with a T tail complementary to the A tail of the completely extended excess adapters (950) to block these excess adapters from being extended. The hairpin adapters however cannot ligate to incompletely extended adaptered nucleic acid fragments (970). Thus, these fragments (970) can be further extended with. In some embodiments, the extension is performed in the presence of a mixture of normal nucleotide and reversible terminators, followed by a reaction to remove the terminator blocking group, and then 3' branch ligation with a BLA (980). This product (990) can now be denatured and separated from the beads and saved for sequencing. The beads can be reused for another round of primer extension with reversible terminators, removal of block group, 3' branch ligation, and denaturation. This process can be repeated multiple times, with varying concentrations of terminators to enable almost complete overlapping DNA coverage of the genomic fragment.

7.2.3 Degrade Excess Adapters

In another embodiment, as disclosed in FIGS. 10A and 10B, controlled extension is performed using a polymerase with 3'-5' exonuclease activity (e.g., Pfu, Q5, Phusion, T7, Vent, Klenow, T4). The extension is limited to about 100-150 bases. Again, the result is that incomplete extension occurs for those adapters ligated to a genomic fragment and complete extension for those excess adapters (i.e., unligated adapters). Because of the 3-5' exonuclease activity of the polymerase, the result is a blunt end dsDNA adapter with a 5' phosphate. This is a perfect substrate for lambda exonuclease while the incomplete extension product for those adaptered fragments are not good substrate for lambda exonuclease. As a result, treatment with lambda exonuclease can be used to degrade all of the unligated excess adapters. The remaining steps that are essentially the same as those depicted in FIGS. 9A and 9B are employed to ligate a second adapter to the genomic fragments.

In yet another embodiment, after the controlled extension that results in complete extension of the unligated adapters and incomplete extension of ligated product (FIG. 11A), controlled extension is continued with reversible terminators added to the reaction. After a period of time, the terminator blocking group is removed from the extension product, and a second adapter is added to the reaction in ligation-permissible condition (e.g., in the presence of a ligase and ligation buffer). FIG. 11B. This results in the blunt end ligation of the excess adapter and 3' branch ligation of the adaptered fragments. At this point a controlled primer extension is performed by extending one strand (1190) of the newly ligated branch ligation adapter using a strand displacing polymerase. As before, this extension is controlled by time, temperature, and/or nucleotide concentration to only extend about 100-150 bases. This extension results in the strand displacement of the first adapter (e.g., the b-BLA) and the release of a copy of dsDNA adapter (1180+1190), which can be separated from the beads and collected. As in the previous examples, the beads can be saved, and this process is repeated to generate overlapping fragments from each adapter ligated to a genomic DNA fragment.

In some embodiments, after the ligated first adapters are extended as described above (e.g., under extension-controlling conditions), a second adapter (FIG. 8, 890) can be ligated to the terminus of the extended product via e.g., blunt ligation or branch ligation.

8. Release

The extended fragments having two adapters one at each terminus are released from the beads. The release from beads can be performed by degrading the beads or by cleaving a chemical linkage between the adapter oligonucleotide and the bead. In some cases, the release is effected by removal of an inosine residue from the capture oligonucleotide using EndoV enzyme or the removal of a uracil nucleotide by uracil deglycosylase and EndoIV/EndoVIII or other enzymes having similar function. In some cases, the capture oligonucleotide is crosslinked to the bead through one or more disulfide bonds. In such cases, the release can be effected by exposing the beads to a reducing agent (e.g., dithiothreitol (DTT) or tris (2-carboxyethyl) phosphine (TCEP)).

9. Amplification

In some embodiments, extended fragments produced in the method steps described above are amplified. Such amplification methods include without limitation: multiple displacement amplification (MDA), polymerase chain reaction (PCR), ligation chain reaction (sometimes referred to as oligonucleotide ligase amplification OLA), cycling probe technology (CPT), strand displacement assay (SDA), transcription mediated amplification (TMA), nucleic acid sequence based amplification (NASBA), rolling circle amplification (RCR) (for circularized fragments), and invasive cleavage technology. Amplification can be performed after fragmenting or before or after any step outlined herein.

In one illustrative example in FIG. 3, the ligated product formed by ligation of the target nucleic acid fragment and the bead adapter and the L-adapter is amplified by annealing primers to the L-adapter and the branch adapter.

In some embodiments, extended fragments can be first denatured into single-stranded nucleic acid molecules. For each of some single-stranded nucleic acid molecules, a splint oligo is then added, which hybridized to the adapter sequences added to the both termini of the target nucleic acid fragments, and the single-stranded nucleic acids are then circularized in the presence of a ligase (e.g., T4 or Taq ligase). The DNA polymerase used for RCR can be any DNA polymerase that has strand-displacement activity, e.g., Phi29, Bst DNA polymerase, Klenow fragment of DNA polymerase I, and Deep-VentR NDA polymerase (NEB #MO258). These DNA polymerases are known to have different strengths of strand-displacement activity. It is within the ability of one of ordinary skill in the art to select one or more suitable DNA polymerase used for the invention.

10. Sequencing

The amplified extended fragments can be sequenced using sequencing methods known in the art, including for example without limitation, polymerase-based sequencing-by-synthesis (e.g., HiSeq 2500 system, Illumina, San Diego, CA), ligation-based sequencing (e.g., SOLID 5500, Life Technologies Corporation, Carlsbad, CA), ion semiconductor sequencing (e.g., Ion PGM or Ion Proton sequencers, Life Technologies Corporation, Carlsbad, CA), zero-mode waveguides (e.g., PacBio RS sequencer, Pacific Biosciences, Menlo Park, CA), nanopore sequencing (e.g., Oxford Nanopore Technologies Ltd., Oxford, United Kingdom), pyrosequencing (e.g., 454 Life Sciences, Branford, CT), or other sequencing technologies. Some of these sequencing technologies are short-read technologies, but others produce longer reads, e.g., the GS FLX+ (454 Life Sciences; up to 1000 bp), PacBio RS (Pacific Biosciences; approximately 1000 bp) and nanopore sequencing (Oxford Nanopore Technologies Ltd.; 100 kb). For haplotype phasing, longer reads are advantageous, requiring much less computation, although they tend to have a higher error rate and errors in such long reads may need to be identified and corrected according to methods set forth herein before haplotype phasing.

According to one embodiment, sequencing is performed using combinatorial probe-anchor ligation (cPAL) as described, for example, in US 20140051588, U.S. 20130124100, both of which are incorporated herein by reference in their entirety for all purposes.

In some embodiments, the fragments that are ligated with the adapters, or amplified products thereof can be denatured to produce single-stranded molecules. A splint oligonucleotide of e.g., 8-40 base, are annealed to both ends of the single-stranded molecules. These annealed oligos enable a 1-10 base overlap between the two ends of the product, similar to the overhangs created after restriction enzyme digestion of plasmid DNA. Ligation can then be performed with T4 DNA ligase to create a single-stranded circle with a small region of double-stranded DNA at the site of ligation. These circles can now be used to make DNA nanoballs (DNBs) for DNBseq sequencers.

In some embodiments, the fragments contain both the b-BLA adapter sequence at the 3' terminus and the L-adapter sequence at the 5' terminus as described above. These adaptered fragments can be sequenced on Illumina type and other systems that do not require circularization.

Compositions

1. Samples

Samples containing target nucleic acids can be obtained from any suitable source. For example, the sample can be obtained or provided from any organism of interest. Such organisms include, for example, plants; animals (e.g., mammals, including humans and non-human primates); or pathogens, such as bacteria and viruses. In some cases, the sample can be, or can be obtained from, cells, tissue, or polynucleotides of a population of such organisms of interest. As another example, the sample can be a microbiome or microbiota. Optionally, the sample is an environmental sample, such as a sample of water, air, or soil.

Samples from an organism of interest, or a population of such organisms of interest, can include, but are not limited to, samples of bodily fluids (including, but not limited to, blood, urine, serum, lymph, saliva, anal and vaginal secretions, perspiration and semen); cells; tissue; biopsies, research samples (e.g., products of nucleic acid amplification reactions, such as PCR amplification reactions); purified samples, such as purified genomic DNA; RNA preparations; and raw samples (bacteria, virus, genomic DNA, etc.). Methods of obtaining target polynucleotides (e.g., genomic DNA) from organisms are well known in the art.

2. Target Nucleic Acid

As used herein, the term “target nucleic acid” (or polynucleotide) or “nucleic acid of interest” refers to any nucleic acid (or polynucleotide) suitable for processing and sequencing by the methods described herein. The nucleic acid may be single-stranded or double-stranded and may include DNA, RNA, or other known nucleic acids. The target nucleic acids may be those of any organism, including but not limited to viruses, bacteria, yeast, plants, fish, reptiles, amphibians, birds, and mammals (including, without limitation, mice, rats, dogs, cats, goats, sheep, cattle, horses, pigs, rabbits, monkeys and other non-human primates, and humans). A target nucleic acid may be obtained from an individual or from a multiple individuals (i.e., a population). A sample from which the nucleic acid is obtained may contain a nucleic acids from a mixture of cells or even organisms, such as: a human saliva sample that includes human cells and bacterial cells; a mouse xenograft that includes mouse cells and cells from a transplanted human tumor; etc. Target nucleic acids may be unamplified or they may be amplified by any suitable nucleic acid amplification method known in the art. Target nucleic acids may be purified according to methods known in the art to remove cellular and subcellular contaminants (lipids, proteins, carbohydrates, nucleic acids other than those to be sequenced, etc.), or they may be unpurified, i.e., include at least some cellular and subcellular contaminants, including without limitation intact cells that are disrupted to release their nucleic acids for processing and sequencing. Target nucleic acids can be obtained from any suitable sample using methods known in the art. Such samples include but are not limited to biosamples such as tissues, isolated cells or cell cultures, bodily fluids (including, but not limited to, blood, urine, serum, lymph, saliva, anal and vaginal secretions, perspiration and semen); and environmental samples, such as air, agricultural, water and soil samples, etc.

Target nucleic acids may be genomic DNA (e.g., from a single individual), cDNA, and/or may be complex nucleic acids, including nucleic acids from multiple individuals or genomes. Examples of complex nucleic acids include a microbiome, circulating fetal cells in the bloodstream of a expecting mother (see, e.g., Kavanagh et al., J. Chromatol. B 878: 1905-1911, 2010), circulating tumor cells (CTC) from the bloodstream of a cancer patient. In one embodiment, such a complex nucleic acid has a complete sequence comprising at least one gigabase (Gb) (a diploid human genome comprises approximately 6 Gb of sequence).

In some cases, target nucleic acids or first complexes are genomic fragments. In some embodiments the genomic fragments are longer than 10 kb, e.g., 10-100 kb, 10-500 kb, 20-300 kb, 50-200 kb, 100-400 kb, or longer than 500 kb. In some cases, target nucleic acids or first complexes are 5,000 to 100,000 Kb in length. The amount of DNA (e.g., human genomic DNA) used in a single mixture may be <10 ng, <3 ng, <1 ng, <0.3 ng, or <0.1 ng of DNA. In some embodiments, the amount of DNA used in the single mixture may be less than 3,000×, e.g., less than 900×, less than 300×, less than 100×, or less than 30× of haploid DNA amount. In some embodiments, the amount of DNA used in the single mixture may be at least 1× of haploid DNA, e.g., at least 2×, or at least 10× haploid DNA amount.

Target nucleic acids may be isolated using conventional techniques, for example as disclosed in Sambrook and Russell, *Molecular Cloning: A Laboratory Manual*, cited supra. In some cases, particularly if small amounts of the nucleic acids are employed in a particular step, it is advantageous to provide carrier DNA, e.g., unrelated circular synthetic double-stranded DNA, to be mixed and used with the sample nucleic acids whenever only small amounts of sample nucleic acids are available and there is danger of losses through nonspecific binding, e.g., to container walls and the like.

According to some embodiments of the invention, genomic DNA or other complex nucleic acids are obtained from an individual cell or small number of cells with or without purification, by any known method.

Long fragments are desirable for the methods of the present invention. Long fragments of genomic DNA can be isolated from a cell by any known method. A protocol for isolation of long genomic DNA fragments from human cells is described, for example, in Peters et al., *Nature* 487:190-195 (2012). In one embodiment, cells are lysed and the intact nuclei are pelleted with a gentle centrifugation step. The genomic DNA is then released through proteinase K and RNase digestion for several hours. The material can be treated to lower the concentration of remaining cellular waste, e.g., by dialysis for a period of time (i.e., from 2-16 hours) and/or dilution. Since such methods need not employ many disruptive processes (such as ethanol precipitation, centrifugation, and vortexing), the genomic nucleic acid remains largely intact, yielding a majority of fragments that have lengths in excess of 150 kilobases. In some embodiments, the fragments are from about 5 to about 750 kilobases in lengths. In further embodiments, the fragments are from about 150 to about 600, about 200 to about 500, about 250 to about 400, and about 300 to about 350 kilobases in length. The smallest fragment that can be used for haplotyping is approximately 2-5 kb; there is no maximum theoretical size, although fragment length can be limited by shearing resulting from manipulation of the starting nucleic acid preparation.

In other embodiments, long DNA fragments are isolated and manipulated in a manner that minimizes shearing or absorption of the DNA to a vessel, including, for example, isolating cells in agarose in agarose gel plugs, or oil, or using specially coated tubes and plates.

According to another embodiment, in order to obtain uniform genome coverage in the case of samples with a small number of cells (e.g., 1, 2, 3, 4, 5, 10, 10, 15, 20, 30, 40, 50 or 100 cells from a microbiopsy or circulating tumor or fetal cells, for example), all long fragments obtained from the cells are barcoded using methods disclosed herein.

3. Barcode

According to one embodiment, a barcode-containing sequence is used that has two, three or more segments of which, one, for example, is the barcode sequence. For example, an introduced sequence may include one or more regions of known sequence and one or more regions of degenerate sequence that serves as the barcode(s) or tag(s). The known sequence (B) may include, for example, PCR primer binding sites, transposon ends, restriction endonuclease recognition sequences (e.g., sites for rare cutters, e.g., Not I, Sac II, Mlu I, BssH II, etc.), or other sequences. The degenerate sequence (N) that serves as the tag is long enough to provide a population of different-sequence tags that is equal to or, preferably, greater than, the number of fragments of a target nucleic acid to be analyzed.

According to one embodiment, the barcode-containing sequence comprises one region of known sequence of any selected length. According to another embodiment the barcode-containing sequence comprises two regions of known sequence of a selected length that flank a region of degenerate sequence of a selected length, i.e., $B_nN_nB_n$, where N may have any length sufficient for tagging long fragments of a target nucleic acid, including, without limitation, N=10, 11, 12, 13, 14, 15, 16, 17, 18, 19 or 20, and B may have any length that accommodates desired sequences such as transposon ends, primer binding sites, etc. For example, such an embodiment may be $B_{20}N_{15}B_{20}$.

In one embodiment, a two or three-segment design is utilized for the barcodes used to tag long fragments. This design allows for a wider range of possible barcodes by allowing combinatorial barcode segments to be generated by ligating different barcode segments together to form the full barcode segment or by using a segment as a reagent in oligonucleotide synthesis. This combinatorial design provides a larger repertoire of possible barcodes while reducing the number of full-size barcodes that need to be generated.

In further embodiments, unique identification of each long fragment is achieved with 8-12 base pair (or longer) barcodes.

In one embodiment, two different barcode segments are used. A and B segments are easily be modified to each contain a different half-barcode sequence to yield thousands of combinations. In a further embodiment, the barcode sequences are incorporated on the same adapter. This can be achieved by breaking the B adapter into two parts, each with a half barcode sequence separated by a common overlapping sequence used for ligation. The two tag components have 4-6 bases each. An 8-base (2×4 bases) tag set is capable of uniquely tagging 65,000 sequences. Both 2×5 base and 2×6 base tags may include use of degenerate bases (i.e., "wildcards") to achieve optimal decoding efficiency.

In further embodiments, unique identification of each sequence is achieved with 8-12 base pair error correcting barcodes. Barcodes may have a length, for illustration and not limitation, of from 5-20 informative bases, usually 8-16 informative bases.

4. UMI

In various embodiments, unique molecular identifiers (UMIs) are used to distinguish individual DNA molecules from one another. For example, UMIs are used to distinguish among the capture oligonucleotides that are immobilized on the first beads. The collection of adapters is generated, each having a UMI, and those adapters are attached to fragments or other source DNA molecules to be sequenced, and the individual sequenced molecules each has a UMI that helps distinguish it from all other fragments. In such implementations, a very large number of different UMIs (e.g., many thousands to millions) may be used to uniquely identify DNA fragments in a sample.

The UMI is at a length that is sufficient to ensure the uniqueness of each and every source DNA molecule. In some embodiments, the unique molecular identifier is about 3-12 nucleotides in length, or 3-5 nucleotides in length. In some cases, each unique molecular identifier is about 3-12 nucleotides in length, or 3-5 nucleotides in length. Thus, a unique molecular identifier can be 3, 4, 5, 6, 7, 8, 9, 10, 11, 12, 13, 14, 15, 16, 17, 18, or more nucleotides in length.

5. Barcoded Beads

The beads are barcoded by the barcode oligonucleotides in the b-BLAs immobilized thereon. Each bead comprises multiple b-BLAs and thus multiple barcode oligonucleotides. Each barcode oligonucleotide comprises at least one barcode. The barcode oligonucleotides on the same bead share the same barcode sequence and barcode oligonucleotides on different beads have different barcode sequences. As such, each bead carries many copies of a unique barcode sequence, which can be transferred to the target nucleic acid fragments using methods as described above.

The beads used may have a diameter in the range of 1-20 μm, alternatively 2-8 μm, 3-6 μm or 1-3 μm, e.g., about 2.8 μm. For example, the spacing of barcoded oligonucleotides on the beads is can at least 1, at least 2, at least 3, at least 4, at least 5, at least 6 or at least 7 nm. In come embodiments the spacing is less than 10 nm (e.g., 5-10 nm), less than 15 nm, less than 20 nm, less than 30 nm, less than 40 nm, or less than 50 nm. In some embodiments, the number of different barcodes used per mixture may be >1M, >10M, >30M, >100M, >300M, or >1B. As discussed below, a very large number of barcodes may be produced for use in the invention, e.g., using methods described herein. In some embodiments, the number of different barcodes are used per mixture may be >1M, >10M, >30M, >100M, >300M, or >1B and they are sampled from a pool of at least 10-fold greater diversity (e.g. from >10M, >0.1 B, 0.3 B, >0.5 B, >1 B, >3 B, >10 B different barcodes on beads.) In some embodiments, the number of barcodes per bead is between 100k to 10M, e.g., between 200k and 1M, between 300k and 800k, or about 400k.

In some embodiments, the barcode region is about 3-15 nucleotides in length, e.g., 5-12, 8-12, or 10 nucleotides in length. In some cases, each barcode of the barcode region is about 3-12 nucleotides in length, or 3-5 nucleotides in length. Thus, a barcode, whether sample barcode, cell barcode or other barcode can be 3, 4, 5, 6, 7, 8, 9, 10, 11, 12, 13, 14, 15 or more nucleotides in length. In one particular example, each barcode region comprises three barcodes, each consisting of 10 bases, and the three barcodes are separated by 6 bases of common sequence.

Barcodes beads are transferred to the target nucleic acid sequence. In some embodiments, the transfer occurred at regular intervals through ligation of the 3' terminus of the adapter oligonucleotide to the nucleic acid fragments created by nicking and the gapping as disclosed.

In some embodiments, the barcoded beads are constructed through a split and pool ligation-based strategy using three sets of double-stranded barcode DNA molecules. In some embodiments, each set of double-stranded barcode DNA molecules consists of 10 base pairs and the three sets are different in nucleic acid sequence. An exemplary method of the split and pool ligation to produce the barcoded beads is described in the PCT Pub. No. WO 2019/217452, the disclosure of which is herein incorporated by reference in its entirety. FIGS. 12 and 13 of WO 2019/217452 also illustrate the methodology of the split and pool method. In one approach, a common adapter sequence comprising a PCR primer annealing site was attached to Dynabeads™ M-280 Streptavidin (ThermoFisher, Waltham, MA) magnetic beads with a 5' dual-biotin linker. Three sets 1,536 of barcode oligos containing regions of overlapping sequence were constructed by Integrated DNA Technologies (Coralville, IA). Ligations were performed in 384 well plates in a 15 μL reaction containing 50 mM Tris-HCl (pH 7.5), 10 mM $MgCl_2$, 1 mM ATP, 2.5% PEG-8000, 571 units T4 ligase, 580 pmol of barcode oligo, and 65 million M-280 beads. Ligation reactions were incubated for 1 hour at room temperature on a rotator. Between ligations beads were pooled into a single vessel through centrifugation, collected to the side of the vessel using magnet, and washed once with high salt wash buffer (50 mM Tris-HCl (pH 7.5), 500 mM NaCl, 0.1 mM EDTA, and 0.05% Tween 20) and twice with low salt wash buffer (50 mM Tris-HCl (pH 7.5), 150 mM NaCl, and 0.05% Tween 20). Beads were resuspended in 1× ligation buffer and distributed across 384 wells plates and the ligation steps were repeated.

In one aspect the invention provides a composition comprising beads with adapter oligonucleotides comprising clonal barcodes attached, where the composition comprises more than 3 billion different barcodes and where the barcodes are tripartate barcodes with the structure 5'-CS1-BC1-CS2-BC2-CS3-BC3-CS4. In some embodiments CS1 and CS4 are loner than CS2 and CS3. In some embodiments CS2 and CS3 are 4-20 bases, CS1 and CS4 are 5 or 10 to 40 bases, e.g., 20-30, and the BC sequences are 4-20 bases (e.g., 10 bases) in length. In some embodiments CS4 is complementary to a splint oligonucleotide. In some embodiments the composition comprises bridge oligonucleotides. In some embodiments the composition comprises bridge oligonucleotides, beads comprising a tripartate barcode as discussed above, and genomic DNA comprising hybridization sequences with a region complementary to the bridge oligonucleotides.

Another source of clonal barcodes such as a bead or other support associated with multiple copies of tags can be prepared by emulsion PCR or CPG (controlled-pore glass) or chemical synthesis other particles with copies of an adapted-barcode prepared by. A population of tag-containing DNA sequences can be PCR amplified on beads in a water-in-oil (w/o) emulsion by known methods. See, e.g., Tawfik and Griffiths Nature Biotechnology 16: 652-656 (1998); Dressman et al., Proc. Natl. Acad. Sci. USA 100: 8817-8820, 2003; and Shendure et al., Science 309:1728-1732 (2005). This results in many copies of each single tag-containing sequence on each bead.

Another method for making a source of clonal barcodes is by oligonucleotide synthesis on micro-beads or CPG in a "mix and divide" combinatorial process. Using this process one can create a set of beads each having population of copies of a barcode. For example, to make all $B_{20}N_{15}B_{20}$ where each of about 1 billion is represented in ~1000+ copies on each of 100 beads, on average, one can start with ~100 billion beads, synthesize $B_{20}$ common sequence (adapter) on all of them and then split them in 1024 synthesis columns to make a different 5-mer in each, then mix them and then split them again in 1024 columns and make additional 5-mer, and then repeat that once again to complete N15, and then mix them and in one big column synthesize the last $B_{20}$ as a second adapter. Thus, in 3050 syntheses one can make the same "clonal-like" sets of barcodes as in one big emulation PCR reaction with ~1000 billion beads ($1^{12}$ beads) because only 1 in 10 beads will have a starting template (the other 9 would have none) to prevent having two templates with different barcode per bead.

An exemplary process for the barcode sequence assembly is described in PCT Pub. No. WO 2019/217452 and the disclosure of which is herein incorporated by reference.

6. Immobilization

Polynucleotides can be immobilized on a substrate (e.g., the beads) by a variety of techniques, including covalent and non-covalent attachment. Polynucleotides can be immobilized to a substrate by a variety of techniques. In some embodiments, a polynucleotide is joined to a substrate (e.g., a bead), that is, one terminus of the polynucleotide directly contacts or is linked to the substrate. For example, a surface may have reactive functionalities that react with complementary functionalities on the polynucleotide molecules to form a covalent linkage. Long DNA molecules, e.g., several nucleotides or larger, may also be efficiently attached to hydrophobic surfaces, such as a clean glass surface that has a low concentration of various reactive functionalities, such as —OH groups. In still another embodiment, polynucleotide molecules can be adsorbed to a surface through non-specific interactions with the surface, or through non-covalent interactions such as hydrogen bonding, van der Waals forces, and the like.

In some embodiments, a polynucleotide is immobilized to a surface through hybridizing to a capture oligonucleotide on the surface and forming complexes, e.g., double-stranded duplexes or partially double-stranded duplexes, with component of the capture oligonucleotide.

7. Reaction Mixture

Provided herein is a reaction mixture comprising one or more nicking agents, one or more ligases, a plurality of beads, a plurality of overlapping nucleic acid fragments separated by staggered single-stranded breaks. Each bead comprises at least one branch ligation adapter immobilized thereon. Each branch ligation adapter comprises a hybridization oligonucleotide and a barcode oligonucleotide. The barcode oligonucleotide comprises a barcode and is joined to the bead, while the hybridization oligonucleotide is not joined to the bead. Each of the plurality of beads comprises a unique barcode sequence, that is, branch ligation adapters on the same bead share the same barcode sequence and branch ligation adapters on different beads have different barcode sequences.

The barcode oligonucleotide is hybridized to the hybridization oligonucleotide to form a partially double-stranded nucleic acid molecule comprising a single-stranded region and a double-stranded region. The double-stranded region comprises a double-stranded blunt end having a 5' terminus and a 3' terminus, and sad 5' terminus of the double-stranded blunt end is ligated to a 3' terminus of a nucleic acid fragment.

Exemplary Embodiments

The following are non-limiting exemplary embodiments of the methods and compositions disclosed herein.

Embodiment 1. A method for preparing a library of adaptered polynucleotides for sequencing, comprising, in a single reaction mixture: (a) contacting a double-stranded target nucleic acid with one or more nicking agents to produce a plurality of overlapping nucleic acid fragments separated by staggered single-stranded breaks; (b) providing a plurality beads each comprising a plurality of branch ligation adapters immobilized on beads (b-BLAs) and providing population of L-adapters with a degenerate sequence at the 3' terminus and (c) contacting the b-BLAs with at least one of the nucleic acid fragments in the presence of a ligase, whereby ligating the b-BLAs to the 3' terminus of the nucleic acid fragments, (d) contact the population of L-adapters in the presence of a ligase thereby ligating the L-adapters to the 5' terminus of the nucleic acid fragments, thereby obtaining a library of nucleic acid fragments having the L-adapter sequence at the 5' terminus and the b-BLA adapter sequence at the 3' terminus, wherein each b-BLA comprises a barcode oligonucleotide, which comprises a b-BLA adapter sequence, and a hybridization oligonucleotide that is hybridized to the barcode oligonucleotide, wherein each L adapter comprises an L-adapter sequence. Optionally, the 3' terminus of hybridization oligonucleotide is a blocker nucleotide.

Embodiment 2. The method of embodiment 1, wherein the 3' terminus of the L-adapter is ligated to the 5' terminus of the at least one of the nucleic acid fragments.

Embodiment 3. The method of embodiment 1, wherein each BLA comprises (i) a double-stranded blunt end comprising a 5' terminus of one strand and a 3' terminus of the complementary strand and (ii) a single-stranded region comprising a barcode sequence, wherein the 5' terminus of the strand in the double-stranded blunt end is ligated to the 3' terminus of the at least one of the nucleic acid fragments via branch ligation.

Embodiment 4. The method of embodiment 1, wherein the method further comprises adding an enzyme to the reaction, wherein the enzyme degrades excess b-BLAs before ligating the L-adapter.

Embodiment 5. The method of embodiment 1, wherein the L-adapter comprises 1-10 degenerated bases at the 3' terminus.

Embodiment 6. The method of embodiment 1, wherein the L-adapter is in solution, wherein the barcode oligonucleotide is joined to the bead, and wherein the hybridization oligonucleotide is not joined to the bead.

Embodiment 7. The method of embodiment 5, wherein the b-BLAs comprises uracil, which can be removed to release the b-BLAs from the bead.

Embodiment 8. The method of embodiment 5, wherein each bead is immobilized thereon with a plurality of b-BLAs and the each of the plurality of b-BLAs has the same barcode sequence.

Embodiment 9. The method of embodiment 1, the method further comprises extending the at least one of the nucleic acid fragments that are ligated with both the b-BLA and L-adapter to produce an extended nucleic acid fragment, wherein the extended nucleic acid fragment comprises a copy of the barcode.

Embodiment 10. The method of embodiment 8, wherein the method further comprises circularizing the extended nucleic acid fragment.

Embodiment 11. The method of embodiment 5, wherein the method comprises a plurality of beads, each comprising a unique barcode sequence.

Embodiment 12. The method of embodiment 1, wherein the 3' terminus of the double-stranded region, or the 3' terminus of the hybridization oligonucleotide, is a dideoxy blocker nucleotide.

Embodiment 13. The method of embodiment 1, wherein average length of the nucleic acid fragments is between 200 nucleotides and 10000 nucleotides.

Embodiment 14. The method of embodiment, wherein greater than 50% of the staggered single-stranded breaks created in step (a) is closed by ligation in step (b).

Embodiment 15. The method of embodiment 1, wherein the one or more nicking agents is selected from the group consisting of a non-specific nicking nuclease, a site-specific nicking nuclease, and a chemical nicking agent.

Embodiment 16. The method of embodiment 1, wherein the non-specific nickase is selected from the group consisting of a Vvn, a Shrimp dsDNA specific endonuclease, and a DNAse 1.

Embodiment 17. The method of embodiment 1, the ligase is T4 DNA ligase.

Embodiment 18. A method for preparing a library of polynucleotides for sequencing comprises in a single reaction mixture:

(a) contacting a double-stranded target nucleic acid with one or more nicking agents to produce overlapping nucleic acid fragments separated by staggered single-stranded breaks; and (b) contacting a bead comprising a plurality of partially double-stranded first adapters with the nucleic acid fragments in the presence of a ligase, wherein each first adapter comprises (i) a double-stranded blunt end comprising a 5' terminus of one strand and a 3' terminus of the complementary strand and (ii) a single-stranded region that is immobilized on a bead, wherein the single-stranded region comprises a barcode, thereby ligating the 5' terminus of the strand in the double-stranded blunt end of at least one first adapters to the 3' terminus of the at least one of the nucleic acid fragments using a DNA ligase to produce a ligated first adapter, wherein the ligated first adapter comprises the barcode and at least one nucleic acid fragment, (c) denaturing the ligated first adapter, and (d) performing a controlled extension of a primer hybridized to a sequence that is 3' relative to the barcode in the ligated first adapter thereby producing a partially extended strand complementary to the ligation first adapter.

Embodiment 19. The method of embodiment 18, wherein at least one of the partially double-stranded first adapters remains unligated, wherein performing the controlled extension comprises hybridizing the primer hybridized to a sequence that is 3' relative to the barcode in both the ligated first adapter and the unligated first adapter, thereby producing a partially extended strand complementary to the ligated first adapter and a fully extended strand complementary to the unligated first adapter, thereby producing a mixture comprising: a partially double-stranded molecule comprising the ligated first adapter, wherein the partially double-stranded molecule comprises a shorter strand and a longer strand, and the double-stranded molecule comprising the unligated adapters.

Embodiment 20. The method of embodiment 19, wherein the method further comprises adding an exonuclease that has double strand DNA exonuclease activity, thereby the exonuclease degrades the double-stranded molecule.

Embodiment 21. The method of embodiment 19, wherein method further comprises adding hairpin adapters to the mixture in step (d) under ligation-permissible conditions thereby double-stranded molecule is ligated to one hairpin adapter and wherein the partially double-stranded molecule remain unligated to the hairpin adapter.

Embodiment 22. The method of embodiment 21 or embodiment 20, wherein the method further comprises: (e) extending the shorter strand in the partially double-stranded molecule strand to copy the sequence of the nucleic acid fragment in the longer strand, thereby producing a further extended strand, and (f) ligating a second adapter to the 3' terminus of further extended strand.

Embodiment 23. The method of embodiment 22, wherein extending the shorter strand in step (e) is performed in the presence of a mixture of extendible nucleotides and nucleotides having 3' reversible blocking groups, wherein the ligating the second adapter in step (f) is performed after removal of the 3' blocking groups.

Embodiment 24. The method of embodiment 23, wherein the nucleotides having 3' reversible blocking groups are added during different cycles.

Embodiment 25. The method of embodiment 23, wherein the second adapter is a branch ligation adapter (BLA).

Embodiment 26. The method of embodiment 23, wherein the method further comprises extending the ligated second branch ligation adapter with a strand displacement polymerase.

Embodiment 27. The method of embodiment any of embodiments 1-26, wherein the target nucleic acid is bound to the bead before the step (a) and step (b).

Embodiment 28. The method of embodiment 27, wherein the method comprises incubating the target nucleic acid with the bead for a period of 0-30 minutes before the nicking in step (a).

Embodiment 29. The method of embodiment 28, wherein the target nucleic acid is incubated with the bead in a buffer comprising 3-12% PEG.

Embodiment 30. The method of any of embodiments 1-26, wherein pH of the single reaction mixture is 7-9.

Embodiment 31. The method of any of embodiments 1-26, wherein the step (a) occurs in the presence of the ligase.

Embodiment 32. The method of embodiment any of embodiments 1-26, wherein the one or more nicking agents and ligases are chosen such that the rate of ligating is higher than the rate of nicking.

Embodiment 33. The method of embodiment 1, wherein the method further comprises after step (b) removing a DNA strand of the first adapter that is not ligated to the nucleic acid fragment by denaturing the reaction mixture.

Embodiment 34. The method of any of embodiments 1-26, wherein step (a) further comprises adding to the single reaction an exonuclease to increase the gap of the staggered single-stranded breaks.

Embodiment 35. The method of embodiment 34, wherein the increased gaps have lengths of 1-30 bases in the staggered single-stranded breaks.

Embodiment 36. A reaction mixture comprising (1) one or more nicking agents, (2) one or more ligases, and (3) a plurality of overlapping nucleic acid fragments separated by staggered single-stranded breaks, and (4) a partially double-stranded branch adapter comprising a barcode oligonucleotide and hybridization oligonucleotide hybridized to each other to form partially double-stranded nucleic acid molecule, wherein the barcode oligonucleotide is joined to a bead and comprises a barcode, wherein the hybridization oligonucleotide is not joined to the bead, wherein the partially double-stranded nucleic acid molecule comprises (i) a double-stranded blunt end having a 5' terminus and a 3' terminus and (ii) a single-stranded region comprising the barcode and having a single-stranded end, wherein the 5' terminus of the double-stranded blunt end is ligated to a 3' terminus of at least one of the nucleic acid fragments.

Embodiment 37. The reaction mixture of embodiment 36, wherein the 5' terminus of the at least one of the nucleic acid fragments is ligated to an L-adapter.

Embodiment 38. The reaction mixture of embodiment 37, wherein the L-adapter comprises 1-10 degenerate bases at the 3' terminus.

Embodiment 39. A method for preparing a library of polynucleotides for sequencing comprises in a single reaction mixture:

(a) contacting a double-stranded target nucleic acid with one or more nicking agents to produce a plurality of overlapping nucleic acid fragments separated by staggered single-stranded breaks; and (b) contacting a partially double-stranded first adapter with at least one of the nucleic acid fragments in the presence of a ligase, wherein the first adapter comprises (i) a double-stranded region having a 5' terminus and a 3' terminus and (ii) a single-stranded region comprising a barcode, thereby joining the 5' terminus of the double-stranded region of the first adapter to the 3' terminus of the at least one of the nucleic acid fragments using a DNA ligase via 3' branch ligation.

(c) contacting a second adapter to the opposite terminus of the at least one of the nucleic acid fragments, wherein ligating the first and second adapters occur in the single reaction.

Embodiment 40. The method of embodiment 39., wherein the second adapter is an L-adapter, wherein the L-adapter comprises a nucleic acid sequence at the 3' terminus that hybridize to a single-stranded region of the target nucleic acid, and wherein the 3' terminus of the L adapter is ligated to the 5' of the at least one of the nucleic acid fragments.

Embodiment 41. The method of embodiment 39., wherein the method further comprises adding an enzyme to the reaction, wherein the enzyme degrades excess first adapter before ligating the second adapter.

Embodiment 42. The method of embodiment 39., wherein the second adapter comprises 1-10 degenerated bases at the 3' terminus.

Embodiment 43. The method of embodiment 39., the method further comprises extending the at least one of the nucleic acid fragments that are joined with one or both of the first and second adapter to produce an extended nucleic acid fragment, wherein the extended nucleic acid fragment comprises a copy of the barcode.

Embodiment 44. The method of embodiment 39., wherein the first adapter is immobilized on a bead via the single-stranded region comprising the barcode, and wherein the bead is immobilized with multiple copies of the first adapters, each comprising the same barcode sequence.

Embodiment 45. The method of embodiment 39., wherein the 3' terminus of the double-stranded region is a dideoxy blocker nucleotide.

Embodiment 46. A method for preparing a library of polynucleotides for sequencing comprises in a single reaction mixture: (a) contacting a double-stranded target nucleic acid with one or more nicking agents to produce overlapping nucleic acid fragments separated by staggered single-stranded breaks; and (b) contacting a bead comprising a plurality of partially double-stranded first adapters with the nucleic acid fragments in the presence of a ligase, wherein each first adapter comprises (i) a double-stranded region having a 5' terminus and a 3' terminus and (ii) a single-stranded region that is immobilized on a bead, wherein the single-stranded region comprises a barcode, thereby joining the 5' terminus of the double-stranded region of at least one of the first adapters to the 3' terminus of the at least one of the nucleic acid fragments using a DNA ligase via 3' branch ligation to produce a ligated first adapter, wherein the ligated first adapter comprises the barcode and at least one nucleic acid fragment, wherein at least one of the first adapters remains as an unligated first adapter, (c) denaturing the reaction mixture, wherein the ligated first adapter and unligated first adapter are in a single-stranded form, (d) performing a controlled extension of a primer hybridized to a sequence that is 3' him relative to the barcode (i) in the ligated first adapter and (ii) in unligated first adapter, thereby producing a partially extended strand complementary to the ligation first adapter and a fully extended strand complementary to the unligated first adapter, thereby producing a first mixture comprising: a partially double stranded molecule comprising the ligated first adapter, and the double stranded molecule comprising the unligated adapters.

Embodiment 47. The method of embodiment 46, wherein the controlled extension is performed with a Tag polymerase, and wherein the method further comprises adding hairpin adapters to the first mixture in step (d) under permissible conditions for ligating the hairpin adapter to the double stranded molecule, thereby producing a second mixture comprising: a double stranded molecule ligated to the hairpin adapter, and a partially double stranded molecule that is not ligated to the hairpin adapter.

Embodiment 48. The method of embodiment 46, wherein the method further comprises adding an exonuclease that has double strand DNA exonuclease activity, thereby the exonuclease degrades the double stranded molecule.

Embodiment 49. The method of clam 47 of embodiment 48, wherein the method further comprises (e) extending the partially extended strand to incorporate the sequence of the nucleic acid fragment to produce a further extended product, and (f) ligating a second branch adapter to the terminus of further extended product.

Embodiment 50. The method of any of the embodiments above, wherein (1) nicking the target nucleic acid and ligating both the b-BLAs and the L-adapters to the nucleic acid fragments last at least 30 minutes, or wherein nicking the double-stranded target nucleic acid and ligating the first adapters to the nucleic acid fragments last at least 30 minutes.

While this invention has been disclosed with reference to specific aspects and embodiments, it is apparent that other embodiments and variations of this invention may be devised by others skilled in the art without departing from the true spirit and scope of the invention.

Each and every publication and patent document cited in this disclosure is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

EXAMPLES

The following examples are provided to illustrate but not to limit the embodiments disclosed in this application.

Example 1 Nick Ligation Protocol Using Segmentase

1. Pre-Binding Genomic DNA to Beads

Barcoded bead stock solutions containing 1 million beads per microliter. The beads were immobilized with branch adapters comprising barcode sequences using methods described in Cheng, et al. 2018, A simple bead-based method for generating cost-effective co-barcoded sequence reads. Protocol Exchange, available at https://doi.org/10.1038/protex.2018.116; Wang, et al. Genome Res. 2019 May; 29(5): 798-808. doi: 10.1101/gr.245126.118. Epub Aprl 2., 2019) were first washed using LSWB buffer (Low Salt Wash Buffer: 0.05 M Tris-HCl pH 7.5, 0.15 M NaCl, and 0.05% Tween 20) twice, and then with 1×HB buffer (3×HB buffer comprise 30% PEG8000, 150 mM Tris-HCl PH 7.8, 30 mM MgCl2, 3 mM ATP, and 0.15 mg/mL BSA, pH 8.3) once.

The branch adapter comprises a barcode oligonucleotide and hybridization oligonucleotide annealed to each other. The 5-terminus of the barcode oligonucleotide has a phosphate group, and the 3-terminus of the hybridization oligonucleotide is a dideoxy nucleotide. The barcode oligonucleotide has a sequence of:

```
/5Phos/GTGCACT*GA*CG*AC*ATGATCACC
AAGGATCGCCATAGTCCATGCTA[Barcode]G
GAAGG[Barcode]CGCAGA[Barcode]CCAG
AGCAACTCCTTGGCTCACAUAAAAAAAAAAAAA
AA/3BioTEG/
(each * represent a phosphothiolate
bond, which are resistant to
nucleases)
```

The hybridization oligonucleotide has a sequence of G*TC*GT*CIGTGC*A*/3 ddC/, in which 3 ddC represents a dideoxy cytosine at the 3 prime.

20 μL 3×HB buffer and water were added to each sample containing about 1 ng genomic DNA, resulting a mixture with a total volume of 45 μL. 30 million beads prepared as above were added to each sample and incubated at room temperature for 15 minutes.

2. Incubation with Single Stranded Binding Protein (SSB)

The SSB mixture was prepared by mixing 4.75 μL (7.5 ug total) of SSB stock solution (Novus Biologicals #NBP2-35314-1 mg) in 10.25 μL 1×HB buffer. The 15 μL SSB mixture was added to the genomic DNA and bead mixture from the previous step and incubated at 37° C. for 15 minutes.

3. Nick-Ligation

An L-oligo, ligase (NEB #M0202T), Segmentase working solutions (a nickase included in the MGIEasy FS PCR-Free DNA Library Prep Set-MGI-Leading Life Science Innovation, MGI, Item number 1000013454 or 1000013455), and Exo III (NEB #M0206S] were prepared by diluting in 1×HB ("Diluted concentration") according to the Table 2 below. The L-oligo has a sequence of GAGACGTTCTCGACTCAGCAGANNNN*N*N*N (N represents any one of A, T, C, G and each * represent a phosphothiolate bond, which are resistant to nucleases).

TABLE 2

| Stock | Buffer | | ul/rxn | Diluted concentration | | Final concentration |
|---|---|---|---|---|---|---|
| 100 uM | none | L-oligo | 3.0 | 100 uM | 300 pmoles/rxn | 4 pmoles/μL |
| 2000 U/ul | 1XHB | NEB Ligase | 6.0 | 100 U/ul | 600 U/rxn | 8.00 U/μL |
| 1.3 U/ul | 1XHB | Segmentase | 3.0 | 0.075 U/ul | 0.0225 U/rxn | 0.003 U/μL |
| 1 U/ul* | 1XHB | ExoIII | 3.0 | 0.025 U/ul | 0.075 U/rxn | 0.001 U/μL |

The prepared L-oligo, ligase, Segmentase, and ExoIII working solutions were added to the 60 μL bead-gDNA mixture, each bead immobilized with branch adapters comprising barcodes, formed above on ice and mixed. The total volume of the reaction mixture was 75 μL. See Table 3.

TABLE 3

| | |
|---|---|
| L-oligo | 3.0 μL |
| T4 Ligase | 6.0 μL |
| Segmentase | 3.0 μL |
| ExoIII | 3.0 μL |
| mix | 60.0 μL |
| total | 75.0 μL |

The reaction mixture was subjected to a condition cycling between 15° C. for 30 seconds and 37° C. for 30 seconds for a total of 54 cycles. The reaction mixture was briefly spun down and placed on a magnet for 2 minutes. The beads in the mixture were then washed with 40 μL of 0.1 M sodium hydroxide. The beads were then washed twice with 100 μL LSWB. The beads were resuspended in 50 μL LSWB and the bead suspension was kept at 4° C. before the PCR amplification, which is further described below.

4. PCR

The LSWB buffer was removed from the beads suspension and the beads were then resuspended in a PCR mixture containing primers PCR1 and PCR2 (sequences below) and 2×KAPA HiFi (Roche #7958935001) to amplify products formed in the nick-ligate reaction. As described in Table 4:

TABLE 4

| PCR set up (on ice) | 1x | Final concentration | |
|---|---|---|---|
| ligation product on beads | 40.0 | | |
| PCR1 (20 uM) | 5.0 | 0.5 | uM |
| PCR2 (20 uM) | 5.0 | 0.5 | UM |
| 2x KAPA HiFi mix | 100.0 | 1 | X |
| H2O | 50.0 | | |
| Total | 200.0 | | |

PCR1 TGTGAGCCAAGGAGTTG (SEQ ID NO: 1)
PCR2 GCCTCCCTCGCGCCATCAG (SEQ ID NO: 2)

PCR cycling was performed according to the condition in Table 5 below:

TABLE 5

| | | |
|---|---|---|
| 95 C. | 3 min | |
| 98 C. | 20 sec | 5 cycles |
| 56 C. | 30 sec | |
| 72 C. | 1 min | |
| 72 C. | 5 min | |
| 4 C. | Hold | |

TABLE 6

| PCR set up (on ice) | 1x | Final concentration | |
|---|---|---|---|
| pur PCR pdt after 5 cycles | 60.0 | | |
| PCR1 (20 uM) | 10.0 | 0.5 | uM |
| PCR2 (20 uM) | 10.0 | 0.5 | uM |
| 2x KAPA HiFi mix | 200.0 | 1x | |
| H2O | 120.0 | | |
| Total | 400.0 | | |

TABLE 7

| | | |
|---|---|---|
| 95 C. | 3 min | |
| 98 C. | 20 sec | 8 cycles |
| 56 C. | 30 sec | |
| 72 C. | 1 min | |
| 72 C. | 5 min | |
| 4 C. | Hold | |

The PCR products were again purified using 0.8× Ampure XP beads (320 ul) using the same steps as above and eluted in 50 ul of TE. The purified products were analyzed by electrophoresis.

Example 2 Effect of the Concentration of Segmentase on Product Size

Nick ligation reactions were performed as described in Example 1, in the presence of different concentrations of Segmentase and T4 DNA ligase as shown in Table 8.

TABLE 8

| | Reaction # | | | | | | | | | |
|---|---|---|---|---|---|---|---|---|---|---|
| | 1 | 2 | 3 | 4 | 5 | 6 | 7 | 8 | 9 | 10 |
| Beads | 30M barcoded beads | 30M barcoded beads | 30M barcoded beads | 30M barcoded beads | 30M barcoded beads | 30M barcoded beads | 30M barcoded beads | 30M barcoded beads | 30M barcoded beads | 30M barcoded beads |
| Buffer | HB buffer, pH 8.3, without DTT | | | | | | | | | |
| gDNA, ng | 1 | 1 | 1 | 1 | 1 | 1 | 1 | 1 | 1 | 1 |
| SSB, ug | 7.50 | 7.50 | 7.50 | 7.50 | 7.50 | 7.50 | 7.50 | 7.50 | 7.50 | 7.50 |
| L-oligo (Ad183_N7P), uM | 4 | 4 | 4 | 4 | 4 | 4 | 4 | 4 | 4 | 4 |
| T4 ligase, NEB, U | 450 | 450 | 450 | 450 | 600 | 600 | 600 | 600 | 900 | 900 |
| Segmentase U/ul | 0.003 | 0.004 | 0.005 | 0.006 | 0.003 | 0.004 | 0.005 | 0.006 | 0.005 | 0.006 |
| ExoIII, U/ul | 0.001 | 0.001 | 0.001 | 0.001 | 0.001 | 0.001 | 0.001 | 0.001 | 0.001 | 0.001 |
| Time | 1.5 hr | 1.5 hr | 1.5 hr | 1.5 hr | 1.5 hr | 1.5 hr | 1.5 hr | 1.5 hr | 1.5 hr | 1.5 hr |

The PCR products were then purified using 0.8× Ampure XP beads (160 μL) (Beckman Coulter #A63881) Beads were washed once in 200 ul of 0.8× Ampure wash buffer (mix 800 ul of fresh Ampure beads and 1 ml of TE, place beads on magnet, collect supernatant, this is the wash buffer). The remain steps were performed according to manufacturer's protocol. The purified product was eluted from the Ampure XP beads in 60 μL of TE buffer. A second round of PCR was performed with the mix and cycling conditions in Tables 6 and 7:

The electrophoresis results of the nick-ligate products (after amplification) are shown in FIG. 12A. The results indicate that increasing amounts of Segmentase resulted in progressively shorter average insert sizes while increasing amounts of T4 DNA ligase resulted in progressively longer average insert sizes. The products formed in these individual reactions #1-#10 had lengths in the range of 300 bp-2 kb and were suitable for sequencing.

Example 3 Nick Ligation Protocol Using Masterase

1. Pre-Binding Genomic DNA to Beads

Pre-binding of genomic DNA to beads immobilized with branch adapters was performed as described in Example 1.

2. Incubation with Single Stranded Binding Protein (SSB)

Incubation of the SSB with genomic DNA and beads were performed as described in Example 1.

3. Nick-Ligation

L-oligo (the same sequence as described in Example 1), ligase (NEB #M0202T), Masterase (Qiagen #EN31-005), and Exo III (NEB #M0206S) were diluted in 1×HB ("Diluted concentration") separately according to the Table 9 below:

TABLE 9

| Stock | Buffer | | ul/rxn | Diluted concentration | | Final concentration |
|---|---|---|---|---|---|---|
| 100 uM | none | L-oligo | 3.0 | 100 uM | 300 pmoles/rxn | 4 pmoles/μL |
| 2000 U/ul | 1XHB | NEB Ligase | 6.0 | 100 U/ul | 600 U/rxn | 8.00 U/μL |
| 1.3 U/ul | 1XHB | Masterase | 5.0 | 0.9 U/ul | 0.0225 U/rxn | 0.06 U/μL |
| 1 U/ul* | 1XHB | ExoIII | 6.0 | 0.125 U/ul | 0.075 U/rxn | 0.01 U/μL |

L-oligo (the same as described in Example 1), ligase, Segmentase, and ExoIII were added to the 55 μL bead-gDNA mixture formed above on ice and mixed. The total volume of the reaction was 75 μL. See Table 3 above.

TABLE 3

| | |
|---|---|
| L-oligo | 3.0 μL |
| T4 Ligase | 6.0 μL |
| Masterase | 5.0 μL |
| ExoIII | 6.0 μL |
| mix | 55.0 μL |
| total | 75.0 μL |

The reaction mixture was to subjecting the reaction to a condition cycling between 10° C. for 30 seconds and 37° C. for 30 seconds for a total of 54 cycles. The reaction mixture was briefly spun down and placed on a magnet for 2 minutes. The beads in the mixture were then washed with 40 μL of 0.1 M sodium hydroxide. The beads were then washed twice with 100 μL LSWB. The beads were resuspended in 50 μL LSWB and the bead suspension was kept at 4° C. before the PCR amplification, which is further described below.

4. PCR

The LSWB buffer was removed from the beads suspension and the beads were then resuspended in a PCR mixture containing primer PCR1 (SEQ ID NO: 1) and 2×KAPA HiFi (Roche #7958935001). As described in the Table 10 below:

TABLE 10

| Primer extension set up (on ice) | 1x | Final concentration | |
|---|---|---|---|
| PCR1 (20 uM) | 2.5 | 0.5 | uM |
| 2x KAPA HiFi mix | 50 | 1 | X |
| H2O | 47.5 | | |
| Total | 100.0 | | |

Primer extension was performed according to the condition in Table 5 above:

The primer extension reaction was placed on a magnetic rack for 2 minutes. The supernatant was collected and the mixture comprising components listed in Table 11 was added:

TABLE 11

| Primer extn. set up (on ice) | 1x | |
|---|---|---|
| PCR2 (20 uM) (SEQ ID NO: 2) | 2.5 | |
| 2x KAPA HiFi mix | 0.5 | |
| Total | 3.0 | ul |

One cycle of extension was performed with the following cycling conditions shown in Table 5.

ExoVII was added to remove any single stranded artifact products using the mix comprising the components below (Table 12) and the reaction was then incubated for 30 minutes.

TABLE 12

| | | |
|---|---|---|
| PCR extension product volume | 103.0 | |
| 0.4M MgCl2 | 2.0 | |
| ExoVII, 0.5 U/ul | 2.0 | |
| Total | 107.0 | ul |

The extension products were then purified using 0.8× Ampure XP beads (85 μL) (Beckman Coulter #A63881) as described above. The purified products were eluted in 60 μL of TE buffer. A final round of PCR was performed with the mix under cycling conditions shown in Table 5, except the PCR was performed for nine cycles.

| PCR set up (on ice) | 1x | Final concentration | |
|---|---|---|---|
| pur PCR pdt after 5 cycles | 40.0 | | |
| PCR1 (20 uM) (SEQ ID NO: 1) | 10.0 | 0.5 | uM |
| PCR2 (20 uM) (SEQ ID NO: 2) | 10.0 | 0.5 | uM |
| 2x KAPA HiFi mix | 200.0 | 1x | |
| H2O | 140.0 | | |
| Total | 400.0 | | |

The PCR products were again purified using 0.8× Ampure XP beads (320 ul) using the same steps as above and eluted in 40 ul of TE. The purified products were analyzed by electrophoresis.

Example 4. Effect of the Concentration of Masterase on Product Size

Nick ligation reactions were performed following the protocols as described in Example 3 in the presence of different concentrations of Masterase and T4 DNA ligase. See the Table 13 below.

TABLE 13

| | Reaction # | | | | | | | |
|---|---|---|---|---|---|---|---|---|
| | 1 | 2 | 3 | 4 | 5 | 6 | 7 | 8 |
| Beads | 30M barcoded beads | 30M barcoded beads | 30M barcoded beads | 30M barcoded beads | 30M barcoded beads | 30M barcoded beads | 30M barcoded beads | 30M barcoded beads |
| gDNA, ng | 1 | 1 | 1 | 1 | 1 | 1 | 1 | 0 |
| Masterase, U/ul | 0.01 | 0.02 | 0.03 | 0.04 | 0.06 | 0.08 | 0.03 | 0.03 |
| SSB, ug | 3.75 | 3.75 | 3.75 | 3.75 | 3.75 | 3.75 | 3.75 | 3.75 |
| ExoIII, U/ul | 0.01 | 0.01 | 0.01 | 0.01 | 0.01 | 0.01 | 0.01 | 0.01 |
| T4 ligase, NEB, Units | 900 | 900 | 900 | 900 | 900 | 900 | 0 | 900 |
| L-oligo Ad183_N7P, uM | 4 | 4 | 4 | 4 | 4 | 4 | 4 | 4 |

The electrophoresis results of the nick ligation products (after amplification) are shown in FIG. 12B. The results indicate that increasing amounts of Masterase resulted in progressively shorter insert lengths. The products formed in reactions #1-#6 had lengths in the range of 300 bp-3 kb and were suitable for sequencing.

Example 5 Two Rounds of Nick Ligation Using Segmentase

1. Pre-Binding Genomic DNA to Beads

Pre-binding of genomic DNA to beads immobilized with branch adapters was performed as described in Example 1.

2. Incubation with Single Stranded Biding Protein (SSB)

Incubation of the SSB with genomic DNA and beads were performed as described in Example 1.

3. Nick-Ligation

L-oligo (the same as described in Example 1), ligase (NEB #MO202T), Segmentase (MGI), and Exo III (NEB #M0206S) were diluted in 1×HB ("Diluted concentration") separately according to the Table 14 below,

TABLE 14

| Stock | Buffer | | ul/rxn | Diluted concentration | | Final concentration |
|---|---|---|---|---|---|---|
| 100 uM | none | L-oligo | 3.0 | 100 uM | 300 pmoles/rxn | 4 pmoles/μL |
| 2000 U/ul | 1XHB | NEB Ligase | 6.0 | 100 U/ul | 600 U/rxn | 8.00 U/μL |
| 1.3 U/ul | 1XHB | Segmentase | 3.0 | 0.100 U/ul | 0.3 U/rxn | 0.004 U/μL |
| 1 U/ul* | 1XHB | ExoIII | 3.0 | 0.025 U/ul | 0.075 U/rxn | 0.001 U/μL |

The L-oligo (the same as described in Example 1), ligase, Segmentase, and ExoIII were added to the 60 μL bead-gDNA mixture formed above on ice and mixed. The total volume of the reaction was 75 μL as described in Example 1.

The reaction mixture was to subjected to a condition cycling between 15° C. for 30 seconds and 37° C. for 30 seconds for a total of 36 cycles. The reaction mixture was briefly spun down and placed on a magnet for 2 minutes. The beads were then washed once with 100 μL LSWB. The beads were resuspended in 60 μL 1×HB.

4. Second L-Oligo Ligation

L-oligo (the same as described in Example 1), ligase (NEB #M0202T), and T7 exo (NEB #M0263S) were diluted in 1×HB ("Diluted concentration") separately according to the Table 15 below:

TABLE 15

| Stock | Buffer | | ul/rxn | Diluted concentration | | Final concentration |
|---|---|---|---|---|---|---|
| 100 uM | none | L-oligo | 3.0 | 100 uM | 300 pmoles/rxn | 4 pmoles/μL |
| 2000 U/ul | 1XHB | NEB Ligase | 6.0 | 150 U/ul | 900 U/rxn | 12.00 U/μL |
| 1 U/ul* | 1XHB | T7 exo | 6.0 | 0.125 U/ul | 0.75 U/rxn | 0.01 U/μL |

L-oligo (as described in Example 1), ligase, and T7 exo were added to the 60 μL of beads from the previous step. The total volume of the reaction was 75 μL. See Table 3 above.

The reaction mixture was to subjected to a condition cycling between 10° C. for 30 seconds and 37° C. for 30 seconds for a total of 36 cycles. The reaction mixture was briefly spun down and placed on a magnet for 2 minutes. The beads were then washed twice with 100 μL LSWB. The beads were resuspended in 60 μL LSWB.

5. PCR

The LSWB buffer was removed from the beads suspension and the beads were then resuspended in a PCR mixture containing primers PCR1 and PCR2 (sequences below) and 2×KAPA HiFi (Roche #7958935001). As described in the Table 16 below:

TABLE 16

| PCR set up (on ice) | 1x | Final concentration | |
|---|---|---|---|
| PCR1 (20 uM) | 5.0 | 0.5 | uM |
| PCR2 (20 uM) | 5.0 | 0.5 | uM |
| 2x KAPA HiFi mix | 100.0 | 1 | X |
| H2O | 90.0 | | |
| Total | 200.0 | | |

PCR cycling was performed according to the condition in Table 5 for 5 cycles. The PCR products were then purified using 0.8× Ampure XP beads (160 μL) as described above. The purified product was eluted in 60 μL of TE buffer. A second round of PCR for 5 cycles was performed with the mix comprising the components in Table 17 and cycling conditions as shown in Table 5.

TABLE 17

| PCR set up (on ice) | 1x | Final concentration | |
|---|---|---|---|
| pur PCR pdt after 5 cycles | 60.0 | | |
| PCR1 (20 uM) | 10.0 | 0.5 | uM |
| PCR2 (20 uM) | 10.0 | 0.5 | uM |
| 2x KAPA HiFi mix | 200.0 | 1 | X |
| H2O | 120.0 | | |
| Total | 400.0 | | |

The PCR products were again purified using 0.8× Ampure XP beads (320 ul) using the same steps as above and eluted in 60 ul of TE. The purified products were analyzed by electrophoresis.

Example 6 Effect of the Concentration of Segmentase on Product Size with the 2 Step Protocol Nick ligation reactions were performed in the presence of different concentrations of Segmentase and T4 DNA ligase following the protocols as described in Example 5. See the Table 18 below.

TABLE 18

| | | 1 | 2 | 3 | 4 | 5 | 6 |
|---|---|---|---|---|---|---|---|
| | beads | 30M barcoded beads | | | | | |
| step1 | Buffer | HB buffer, pH 8.3, without DTT | | | | | |
| | gDNA, ng | 1 | 1 | 1 | 1 | 1 | 1 |
| | Novus Bio SSB, ug | 7.5 | 7.5 | 7.5 | 7.5 | 7.5 | 7.5 |
| | L-oligo (Ad183_N7P), uM | 4 | 4 | 4 | 4 | 4 | 4 |
| | T4 ligase, NEB, U | 600 | 600 | 600 | 600 | 600 | 600 |

TABLE 18-continued

| | | 1 | 2 | 3 | 4 | 5 | 6 |
|---|---|---|---|---|---|---|---|
| | beads | 30M barcoded beads | | | | | |
| | Segmentase U/ul | 0.004 | 0.005 | 0.006 | 0.007 | 0.008 | 0.009 |
| | ExoIII, U/ul | 0.01 | 0.01 | 0.01 | 0.01 | 0.01 | 0.01 |
| | T7 Exo, U/ul | — | — | — | — | — | — |
| | Time | 1 hr | 1 hr | 1 hr | 1 hr | 1 hr | 1 hr |
| | | wash twice with LSWB | | | | | |
| step2 | Buffer | HB buffer, pH 8.3 | | | | | |
| | L-oligo (Ad183_N7P), uM | 4 | 4 | 4 | 4 | 4 | 4 |
| | T7 Exo, U/ul | 0.01 | 0.01 | 0.01 | 0.01 | 0.01 | 0.01 |
| | T4 Ligase, NEB, U | 900 | 900 | 900 | 900 | 900 | 900 |
| | Time | 1 hr | 1 hr | 1 hr | 1 hr | 1 hr | 1 hr |

The electrophoresis results of the nick ligation products (after amplification) are shown in FIG. 12C.

The results indicate that increasing amounts of Segmentase result in progressively shorter insert lengths and the fragments are formed in these reactions were suitable for sequencing.

Example 7 Two Rounds of Nick Ligation Using Masterase

1. Pre-Binding Genomic DNA to Beads

Barcoded bead stock solutions containing 1 million beads per microliter (see (Cheng, et al. 2018; Wang, et al. 2019) for a description and protocol for making beads) were first washed using LSWB buffer (Low Salt Wash Buffer: 0.05 M Tris-HCl PH 7.5, 0.15 M NaCl, and 0.05% Tween 20) twice, and then with 1×HB buffer (3×HB: 30% PEG8000, 150 mM Tris-HCl pH 7.8, 30 mM MgCl2, 3 mM ATP, and 0.15 mg/mL BSA, pH 8.3) once.

20 μL 3×HB buffer and water were added to each sample containing about 1 ng genomic DNA, resulting a mixture with a total volume of 45 μL. 30 million beads prepared as above were added to each sample and incubated at room temperature for 15 minutes.

2. Incubation with Single Stranded Biding Protein (SSB)

The SSB reaction was prepared by mixing 2.37 μL (3.75 ug total) of SSB stock solution in 7.63 μL 1×HB buffer to produce 10 μL SSB mixture. The 10 μL SSB mixture was added to the genomic DNA and bead mixture from the previous step and incubated at 37° C. for 15 minutes.

3. Nick-Ligation

L-oligo, ligase (NEB #M0202T), Masterase (Qiagen #EN31-005), and Exo III (NEB #M0206S) were diluted in 1×HB ("Diluted concentration") separately according to the Table 19.

TABLE 19

| Stock | Buffer | | ul/rxn | Diluted concentration | | Final concentration |
|---|---|---|---|---|---|---|
| 100 uM | none | L-oligo | 3.0 | 100 uM | 300 pmoles/rxn | 4 pmoles/μL |
| 2000 U/ul | 1XHB | NEB Ligase | 6.0 | 150 U/ul | 900 U/rxn | 12.00 U/μL |
| 1.3 U/ul | 1XHB | Masterase | 5.0 | 1.20 U/ul | 6 U/rxn | 0.08 U/μL |
| 1 U/ul* | 1XHB | ExoIII | 3.0 | 0.125 U/ul | 0.75 U/rxn | 0.01 U/μL |

L-oligo (as described in Example 1), ligase, Segmentase, and ExoIII were added to the 55 μL bead-gDNA mixture formed above on ice and mixed. The total volume of the reaction was 75 μL. See Table 3.

The reaction mixture was subjected to a condition cycling between 10° C. for 30 seconds and 37° C. for 30 seconds for a total of 36 cycles. The reaction mixture was briefly spun down and placed on a magnet for 2 minutes. The beads were then washed once with 100 μL LSWB. The beads were resuspended in 60 μL 1×HB.

4. Second L-Oligo Ligation

L-oligo (as described in Example 1), ligase (NEB #MO202T), and T7 exo (NEB #M0263S) were diluted in 1×HB ("Diluted concentration") separately according to Table 20 below.

TABLE 20

| Stock | Buffer | | ul/rxn | Diluted concentration | | Final concentration |
|---|---|---|---|---|---|---|
| 100 uM | none | L-oligo | 3.0 | 100 uM | 300 pmoles/rxn | 4 pmoles/μL |
| 2000 U/ul | 1XHB | NEB Ligase | 6.0 | 150 U/ul | 900 U/rxn | 12.00 U/μL |
| 1 U/ul* | 1XHB | T7 exo | 6.0 | 0.125 U/ul | 0.75 U/rxn | 0.01 U/μL |

L-oligo (as described in Example 1), ligase, and T7 exo were added to the 60 μL of beads from the previous step. The total volume of the reaction was 75 μL as show in Table 3:

The reaction mixture was subjected to a condition cycling between 10° C. for 30 seconds and 37° C. for 30 seconds for a total of 36 cycles. The reaction mixture was briefly spun down and placed on a magnet for 2 minutes. The beads were then washed twice with 100 μL LSWB. The beads were resuspended in 60 μL LSWB.

5. PCR

The LSWB buffer was removed from the beads suspension and the beads were then resuspended in a PCR mixture containing primers PCR1 and PCR2 (sequences below) and 2×KAPA HiFi (Roche #7958935001). As described in the Table 21 below:

TABLE 21

| PCR set up (on ice) | 1x | Final concentration | |
|---|---|---|---|
| PCR1 (20 uM) | 5.0 | 0.5 | uM |
| PCR2 (20 uM) | 5.0 | 0.5 | uM |
| 2x KAPA HiFi mix | 100.0 | 1 | X |
| H2O | 90.0 | | |
| Total | 200.0 | | |

PCR cycling was performed according to the condition in Table 5 below:

The PCR products were then purified using 0.8× Ampure XP beads (160 μL) (Beckman Coulter #A63881) Beads were washed once in 200 ul of 0.8× Ampure wash buffer (mix 800 ul of fresh Ampure beads and 1 ml of TE, place beads on magnet, collect supernatant, this is the wash buffer). The remain steps were performed according to manufacturer's protocol. and the product was eluted in 60 μL of TE buffer. A second round of PCR was performed with the mix comprising the ingredients in Table 22 and cycling conditions as show in Table 5, except that the PCR was performed for seven cycles.

TABLE 22

| PCR set up (on ice) | 1x | Final concentration | |
|---|---|---|---|
| pur PCR pdt after 5 cycles | 60.0 | | |
| PCR1 (20 uM) | 10.0 | 0.5 | uM |
| PCR2 (20 uM) | 10.0 | 0.5 | uM |
| 2x KAPA HiFi mix | 200.0 | 1 | X |
| H2O | 120.0 | | |
| Total | 400.0 | | |

The PCR products were again purified using 0.8× Ampure XP beads (320 ul) using the same steps as above and eluted in 60 ul of TE. The purified products were analyzed by electrophoresis.

Example 8 Effect of the Concentration of Masterase on Product Size with the 2 Step Protocol Nick ligation reactions were performed in the presence of different concentrations of Masterase and T4 DNA ligase following the protocols as described in Example 7. See the Table 23 and Table 24 below.

TABLE 23

| | | Sample | | | |
|---|---|---|---|---|---|
| | | 1 | 2 | 3 | 4 |
| Ligation 1 | HB buffer pH 8.3 | no DTT | no DTT | no DTT | no DTT |
| | gDNA, ng | 1 | 1 | 1 | 1 |
| | Masterase, U/ul | 0.06 | 0.07 | 0.07 | 0.08 |
| | Creative Biomart SSB, ug total | 3.75 | 3.75 | 3.75 | 3.75 |
| | ExoIII, U/ul | 0.01 | 0.01 | 0.01 | 0.01 |
| | NEB T4 ligase | 600 | 600 | 900 | 900 |
| | L-oligo Ad183_N7P uM | 4 | 4 | 4 | 4 |
| | Reaction | 10 C./37 C., X36* | | | |

TABLE 24

| | | wash with LSWB Sample | | | |
|---|---|---|---|---|---|
| | | 1 | 2 | 3 | 4 |
| Ligation 2 | L-oligo Ad183_N7P uM | 4 | 4 | 4 | 4 |
| | HB buffer pH 8.3 | std | std | std | std |
| | T7 Exo, U/ul | 0.01 | 0.01 | 0.01 | 0.01 |
| | NEB T4 ligase | 600 | 600 | 900 | 900 |
| | Reaction | 10 C./37 C., X36* | | | |

As described in the examples, e.g., in Tables 23 and 24, "10 C/37 C, ×36" refers to subjecting the reaction to a condition cycling between 10° C. for 30 seconds and 37° C. for 30 seconds for a total of 36 cycles.

The electrophoresis results of the nick ligation products (after amplification) indicate that increasing amounts of Masterase result in progressively shorter insert lengths and increasing amounts of T4 ligase result in progressively longer insert lengths. The fragments are formed in these reactions were suitable for sequencing See FIG. 12D.

What is claimed is:

1. A method for preparing a library of adaptered polynucleotides for sequencing, comprising, in a single reaction mixture: contacting a double-stranded target nucleic acid with one or more nicking agents to produce a plurality of overlapping nucleic acid fragments separated by staggered single-stranded breaks;

(a) providing a plurality of beads each comprising a plurality of branch ligation adapters immobilized on beads (b-BLAs) and providing population of L-adapters with a degenerate sequence at the 3' terminus, wherein each b-BLA comprises a barcode oligonucleotide, which comprises a b-BLA adapter sequence, and a hybridization oligonucleotide that is hybridized to the barcode oligonucleotide, wherein each L adapter comprises an L-adapter sequence, (b) contacting the b-BLAs with at least one of the nucleic acid fragments in the presence of a ligase, whereby ligating the b-BLAs to the 3' terminus of the nucleic acid fragments, and (c) contact the population of L-adapters in the presence of a ligase thereby ligating the L-adapters to the 5' terminus of the nucleic acid fragments, thereby obtaining a library of nucleic acid fragments having the L-adapter sequence at the 5' terminus and the b-BLA adapter sequence at the 3' terminus.

2. The method of claim 1, wherein the 3' terminus of the L-adapter is ligated to the 5' terminus of the at least one of the nucleic acid fragments.

3. The method of claim 1, wherein each BLA comprises (i) a double-stranded blunt end comprising a 5' terminus of one strand and a 3' terminus of the complementary strand and (ii) a single-stranded region comprising a barcode sequence, wherein the 5' terminus of the strand in the double-stranded blunt end is ligated to the 3' terminus of the at least one of the nucleic acid fragments via branch ligation.

4. The method of claim 1, wherein the method further comprises adding an enzyme to the reaction mixture, wherein the enzyme degrades excess b-BLAs before ligating the L-adapter.

5. The method of claim 1, wherein the L-adapter comprises 1-10 degenerated bases at the 3' terminus.

6. The method of claim 1, wherein the L-adapter is in solution, wherein the barcode oligonucleotide is joined to the bead, wherein the hybridization oligonucleotide is not joined to the bead.

7. The method of claim 5, wherein the b-BLAs comprise uracil, which can be removed to release the b-BLAs from the bead.

8. The method of claim 5, wherein each bead is immobilized thereon with a plurality of b-BLAs and the each of the plurality of b-BLAs has the same barcode sequence.

9. The method of claim 1, the method further comprises extending the at least one of the nucleic acid fragments that are ligated with both the b-BLA and L-adapter to produce an extended nucleic acid fragment, wherein the extended nucleic acid fragment comprises a copy of the barcode.

10. The method of claim 8, wherein the method further comprises circularizing the extended nucleic acid fragment.

11. The method of claim 5, wherein the method comprises a plurality of beads, each comprising a unique barcode sequence.

12. The method of claim 1, wherein the 3' terminus of the double-stranded region is a dideoxy blocker nucleotide.

13. The method of claim 1, wherein average length of the nucleic acid fragments is between 200 nucleotides and 10000 nucleotides.

14. The method of claim 1, wherein greater than 50% of the staggered single-stranded breaks created in step (a) is closed by ligation in step (b).

15. The method of claim 1, wherein the one or more nicking agents is selected from the group consisting of a non-specific nicking nuclease, a site-specific nicking nuclease, and a chemical nicking agent.

16. The method of claim 1, wherein the non-specific nickase is selected from the group consisting of a Vvn, a Shrimp dsDNA specific endonuclease, and a DNAse I, and/or the ligase is T4 DNA ligase.

17. A method for preparing a library of polynucleotides for sequencing comprises in a single reaction mixture:

(a) contacting a double-stranded target nucleic acid with one or more nicking agents to produce overlapping nucleic acid fragments separated by staggered single-stranded breaks; and (b) contacting a bead comprising a plurality of partially double-stranded first adapters with the nucleic acid fragments in the presence of a ligase, wherein each first adapter comprises (i) a double-stranded blunt end comprising a 5' terminus of one strand and a 3' terminus of the complementary strand and (ii) a single-stranded region that is immobilized on a bead, wherein the single-stranded region comprises a barcode, thereby ligating the 5' terminus of the strand in the double-stranded blunt end of at least one first adapters to the 3' terminus of the at least one of the nucleic acid fragments using a DNA ligase to produce a ligated first adapter, wherein the ligated first adapter comprises the barcode and at least one nucleic acid fragment, (c) denaturing the ligated first adapter (d) performing a controlled extension of a primer hybridized to a sequence that is 3' relative to the barcode in the ligated first adapter thereby producing a partially extended strand complementary to the ligation first adapter.

18. The method of claim 17, wherein at least one of the partially double-stranded first adapters remains unligated, wherein performing the controlled extension comprises hybridizing the primer hybridized to a sequence that is 3' relative to the barcode in both the ligated first adapter and the unligated first adapter, thereby producing a partially extended strand complementary to the ligated first adapter and a fully extended strand complementary to the unligated first adapter, thereby producing a mixture comprising:

a partially double-stranded molecule comprising the ligated first adapter, wherein the partially double-stranded molecule comprises a shorter strand and a longer strand, and a double-stranded molecule comprising the unligated adapters.

19. The method of claim 18, wherein the method further comprises adding an exonuclease that has double strand DNA exonuclease activity, thereby the exonuclease degrades the double-stranded molecule.

20. The method of claim 18, wherein method further comprises adding hairpin adapters to the mixture in step (d) under ligation-permissible conditions thereby double-stranded molecule is ligated to one hairpin adapter and wherein the partially double-stranded molecule remain unligated to the hairpin adapter.

21. The method of claim 19, wherein the method further comprises:

(a) extending the shorter strand in the partially double-stranded molecule strand to copy the sequence of the nucleic acid fragment in the longer strand, thereby producing a further extended strand, and (b) ligating a second adapter to the 3' terminus of further extended strand.

22. The method of claim 21, wherein extending the shorter strand in step (e) is performed in the presence of a mixture of extendible nucleotides and nucleotides having 3' reversible blocking groups, wherein the ligating the second adapter in step (f) is performed after removal of the 3' blocking groups.

23. The method of claim 22, wherein the nucleotides having 3' reversible blocking groups are added during different cycles, and/or the second adapter is a branch ligation adapter (BLA).

24. The method of claim 22, wherein the method further comprises extending the ligated second branch ligation adapter with a strand displacement polymerase.

25. The method of claim 1, wherein the target nucleic acid is bound to the bead before the step (a) and step (b), wherein the step (a) occurs in the presence of the ligase, and/or wherein the one or more nicking agents and ligases are chosen such that the rate of ligating is higher than the rate of nicking.

26. The method of claim 25, wherein the method comprises incubating the target nucleic acid with the bead for a period of 0-30 minutes before the nicking in step (a).

27. The method of claim 26, wherein the target nucleic acid is incubated with the bead in a buffer comprising 3-12% PEG.

28. The method of claim 1, wherein pH of the single reaction mixture is 7-9.

29. The method of claim 1, wherein the method further comprises after step (b) removing a DNA strand of the first adapter that is not ligated to the nucleic acid fragment by denaturing the reaction mixture.

30. The method claim 1, wherein step (a) further comprises adding to the single reaction mixture an exonuclease to increase the gap of the staggered single-stranded breaks.

31. The method of claim 30, wherein the increased gap has a length of 1-30 bases.

32. The method of claim 1, wherein nicking the target nucleic acid and ligating the b-BLAs and the L-adapters to the nucleic acid fragments last at least 30 minutes.

33. The method of claim 17, wherein nicking the double-stranded target nucleic acid and ligating the first adapters to the nucleic acid fragments last at least 30 minutes.

34. A reaction mixture comprising (1) one or more nicking agents, (2) one or more ligases, (3) a plurality of overlapping nucleic acid fragments separated by staggered single-stranded breaks, (4) a partially double-stranded branch adapter comprising a barcode oligonucleotide and hybridization oligonucleotide hybridized to each other to form partially double-stranded nucleic acid molecule, wherein the barcode oligonucleotide is joined to a bead and comprises a barcode, wherein the hybridization oligonucleotide is not joined to the bead, wherein the partially double-stranded nucleic acid molecule comprises (b) a double-stranded blunt end having a 5' terminus and a 3' terminus and (ii) a single-stranded region comprising the barcode and having a single-stranded end, wherein the 5' terminus of the double-stranded blunt end is ligated to a 3' terminus of at least one of the overlapping nucleic acid fragments.

35. The reaction mixture of claim 34, wherein the 5' terminus of the at least one of the nucleic acid fragments is ligated to an L-adapter.

36. The reaction mixture of claim 34, wherein the L-adapter comprises 1-10 degenerate bases at the 3' terminus.

37. The method of claim 20, wherein the method further comprises:

(a) extending the shorter strand in the partially double-stranded molecule strand to copy the sequence of the nucleic acid fragment in the longer strand, thereby producing a further extended strand, and (b) ligating a second adapter to the 3' terminus of further extended strand.

* * * * *